US012642452B2

(12) United States Patent (10) Patent No.: US 12,642,452 B2
Matsumoto et al. (45) Date of Patent: Jun. 2, 2026

(54) ACTION STATE ESTIMATION APPARATUS, ACTION STATE ESTIMATION METHOD, ACTION STATE LEARNING APPARATUS, AND ACTION STATE LEARNING METHOD

(71) Applicant: Murata Manufacturing Co., Ltd., Nagaokakyo (JP)

(72) Inventors: Tatsuhiko Matsumoto, Nagaokakyo (JP); Atsushi Naito, Nagaokakyo (JP); Naoki Kawara, Nagaokakyo (JP); Yutaka Takamaru, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 500 days.

(21) Appl. No.: 18/156,565

(22) Filed: Jan. 19, 2023

(65) Prior Publication Data

US 2023/0148906 A1 May 18, 2023

Related U.S. Application Data

(63) Continuation of application No. PCT/JP2021/027255, filed on Jul. 21, 2021.

(30) Foreign Application Priority Data

| Jul. 30, 2020 | (JP) | ................................. | 2020-129387 |
| Jul. 30, 2020 | (JP) | ................................. | 2020-129388 |

(51) Int. Cl.
*A61B 5/11* (2006.01)
*A61B 5/00* (2006.01)
(52) U.S. Cl.
CPC .......... *A61B 5/1107* (2013.01); *A61B 5/1101* (2013.01); *A61B 5/7264* (2013.01); *A61B 5/7267* (2013.01)

(58) Field of Classification Search
CPC ... A61B 5/1107; A61B 5/1101; A61B 5/7264; A61B 5/7267
(Continued)

(56) References Cited

U.S. PATENT DOCUMENTS

| 7,623,944 B2 * | 11/2009 | Dariush | ............... | A61B 5/4528 |
| | | | | 318/560 |
| 9,402,579 B2 * | 8/2016 | McLeod | ................ | A61B 5/224 |

(Continued)

FOREIGN PATENT DOCUMENTS

| JP | 200278697 A | 3/2002 |
| JP | 2003116822 A | 4/2003 |

(Continued)

OTHER PUBLICATIONS

International Search Report in PCT/JP2021/027254, mailed Oct. 12, 2021, 4 pages.

(Continued)

*Primary Examiner* — Allen Chan
(74) *Attorney, Agent, or Firm* — ArentFox Schiff LLP

(57) ABSTRACT

An action state estimation apparatus is provided that includes a sampling portion, an action state model storage, and an estimation calculation portion. The sampling portion samples a displacement measurement signal within a predetermined time and generates displacement measurement data based on the sampled displacement measurement signal. The action state model storage stores an action state model modeled by associating the displacement measurement data with a loaded state of a muscle of the test subject. The estimation calculation portion then estimates the loaded state by setting the displacement measurement data as an input vector and using the action state model.

14 Claims, 25 Drawing Sheets

(58) Field of Classification Search
USPC ........................................................... 700/91
See application file for complete search history.

(56) References Cited

U.S. PATENT DOCUMENTS

| | | | |
|---|---|---|---|
| 11,617,527 B2 * | 4/2023 | Majava ................ | A61B 5/1123 |
| | | | 482/8 |
| 12,011,257 B2 * | 6/2024 | Matijevich ............. | A61B 5/746 |
| 2017/0043215 A1 | 2/2017 | Peterson et al. | |
| 2021/0366602 A1 | 11/2021 | Huang et al. | |

FOREIGN PATENT DOCUMENTS

| | | | |
|---|---|---|---|
| JP | 2006345990 A | 12/2006 |
| JP | 2007160076 A | 6/2007 |
| JP | 2011182824 A | 9/2011 |
| JP | 201697228 A | 5/2016 |
| JP | 2017-023449 A | 2/2017 |
| JP | 201842998 A | 3/2018 |
| WO | 2019/130840 A1 | 7/2019 |

OTHER PUBLICATIONS

International Search Report in PCT/JP2021/027255, mailed Oct. 12, 2021, 4 pages.
Takanokura et al., "Mechanism of physiological tremor in upper limb and its application for evaluation of fatigue," The University of Electro-Communications, 2001, vol. 37, Retrieved from the Internet: <URL: https://www.jstage.jst.go.p/article/je 1965/37/Supplement/37_Supplement_274/_article/-char/ja/>, pp. 274-275.

* cited by examiner

| LEVEL OF IMPORTANCE | MUCLE M1 | MUCLE M2 | MUCLE M3 | MUCLE M4 |
|---|---|---|---|---|
| 1ST | A1 | A3 | A5 | A4 |
| 2ND | A2 | A5 | A13 | A11 |
| 3RD | A8 | A2 | A3 | A1 |
| 4TH | A12 | A14 | A2 | A3 |
| 5TH | A7 | A15 | A9 | A6 |

| TIME | t1 | t2 | t3 | t4 | · · · · · | t98 | t99 | t100 |
|---|---|---|---|---|---|---|---|---|
| SIGNAL STRENGTH | 1.5 | 1.9 | 4.2 | 0.3 | · · · · · | 3.6 | 2.0 | 1.3 |

FIG.6B

| RANK | R1 | R2 | R3 | R4 | · · · · · | R98 | R99 | R100 |
|---|---|---|---|---|---|---|---|---|
| SIGNAL STRENGTH | 4.2 | 4.0 | 4.0 | 3.6 | · · · · · | 0.4 | 0.4 | 0.3 |

FIG.6C

| STRENGTH BLOCK | B1 | B2 | B3 | · · · · · | B9 | B10 |
|---|---|---|---|---|---|---|
| INTEGRATED VALUE | 40.2 | 33.5 | 21.8 | · · · · · | 15.2 | 6.7 |

| LEVEL OF IMPORTANCE | MUSCLE M1 | MUSCLE M2 | MUSCLE M3 | MUSCLE M4 |
|---|---|---|---|---|
| 1ST | B10 | B10 | B3 | B7 |
| 2ND | B9 | B8 | B8 | B6 |
| 3RD | B6 | B9 | B1 | B10 |
| 4TH | B3 | B7 | B2 | B8 |
| 5TH | B5 | B1 | B10 | B9 |

| TIME | t1 | t2 | t3 | · · · | t10 | · · · | t91 | · · · | t99 | t100 |
|---|---|---|---|---|---|---|---|---|---|---|
| SIGNAL STRENGTH | 1.5 | 1.9 | 4.2 | · · · | 0.3 | · · · | 2.6 | · · · | 2.0 | 1.3 |

FIG.8B

| TIME BLOCK | B1t | B2t | B3t | · · · · · | B9t | B10t |
|---|---|---|---|---|---|---|
| AVERAGE VALUE | 3.01 | 2.23 | 1.42 | · · · · · | 1.28 | 2.13 |

FIG.8C

| TIME BLOCK | B1t | B2t | B3t | · · · · · | B9t | B10t |
|---|---|---|---|---|---|---|
| INTEGRATED VALUE | 30.1 | 22.3 | 14.2 | · · · · · | 12.8 | 21.3 |

FIG.10A

| LEVEL OF IMPORTANCE | MUSCLE M1 | MUSCLE M2 | MUSCLE M3 | MUSCLE M4 |
|---|---|---|---|---|
| 1ST | Ar1 | Ar3 | Ar5 | Ar4 |
| 2ND | Ar2 | Ar5 | Ar13 | Ar11 |
| 3RD | Ar8 | Ar2 | Ar3 | Ar1 |
| 4TH | Ar12 | Ar14 | Ar2 | Ar3 |
| 5TH | Ar7 | Ar15 | Ar9 | Ar6 |

FIG.10B

| LEVEL OF IMPORTANCE | MUSCLE M1 | MUSCLE M2 | MUSCLE M3 | MUSCLE M4 |
|---|---|---|---|---|
| 1ST | Aa1 | Aa3 | Aa5 | Aa4 |
| 2ND | Aa2 | Aa5 | Aa13 | Aa11 |
| 3RD | Aa8 | Aa2 | Aa3 | Aa1 |
| 4TH | Aa12 | Aa14 | Aa2 | Aa3 |
| 5TH | Aa7 | Aa15 | Aa9 | Aa6 |

FIG.14A

| LEVEL OF IMPORTANCE | MUSCLE M1 | MUSCLE M2 | MUSCLE M3 | MUSCLE M4 |
|---|---|---|---|---|
| 1ST | Br10 | Br10 | Br3 | Br7 |
| 2ND | Br9 | Br8 | Br8 | Br6 |
| 3RD | Br6 | Br9 | Br1 | Br10 |
| 4TH | Br3 | Br7 | Br2 | Br8 |
| 5TH | Br5 | Br1 | Br10 | Br9 |

FIG.14B

| LEVEL OF IMPORTANCE | MUSCLE M1 | MUSCLE M2 | MUSCLE M3 | MUSCLE M4 |
|---|---|---|---|---|
| 1ST | Ba10 | Ba10 | Ba3 | Ba7 |
| 2ND | Ba9 | Ba8 | Ba8 | Ba6 |
| 3RD | Ba6 | Ba9 | Ba1 | Ba10 |
| 4TH | Ba3 | Ba7 | Ba2 | Ba8 |
| 5TH | Ba5 | Ba1 | Ba10 | Ba9 |

|  | B1t | B2t | B3t | B4t |
|---|---|---|---|---|
| MUSCLE M1 (VICINITY OF SENSOR) | HIGH IMPORTANCE | LOW IMPORTANCE | LOW IMPORTANCE | HIGH IMPORTANCE |
| MUSCLE M2 (AWAY FROM SENSOR) | LOW IMPORTANCE | HIGH IMPORTANCE | HIGH IMPORTANCE | LOW IMPORTANCE |

ACTION STATE ESTIMATION APPARATUS, ACTION STATE ESTIMATION METHOD, ACTION STATE LEARNING APPARATUS, AND ACTION STATE LEARNING METHOD

CROSS REFERENCE TO RELATED APPLICATIONS

This application is a continuation of PCT Application No. PCT/JP2021/027255, filed Jul. 21, 2021, which claims priority to Japanese Patent Application No. 2020-129387, filed Jul. 30, 2020, and Japanese Patent Application No. 2020-129388, filed Jul. 30, 2020, the entire contents of each of which are hereby incorporated by reference in their entirety.

TECHNICAL FIELD

The present invention relates to a system and method for estimating an action state including a loaded state of a muscle from a detection result of a tremor and a system and method (e.g., an action state learning technology) of generating an action state model for such an estimation technology.

BACKGROUND

Japanese Patent Application Publication No. 2011-182824 (hereinafter "Patent Literature 1") discloses an action state estimation apparatus that converts a measurement signal of a displacement detection sensor into a frequency component. The action state estimation apparatus disclosed in Patent Literature 1 estimates an action state from a component of a predetermined frequency band.

However, conventional apparatus and method that are shown in Patent Literature 1 need to convert a measurement signal of a sensor into a frequency component. Therefore, a processing load to generate a signal for estimation increases.

SUMMARY OF THE INVENTION

Therefore, it is an object of the present invention to provide an action state estimation system and method that significantly reduces a processing load while achieving a desired estimation accuracy.

In an exemplary aspect, an action state estimation apparatus is provided that includes a first sampling portion, an action state model storage, and an estimation calculation portion. The first sampling portion samples a displacement measurement signal within a predetermined time and generates displacement measurement data. The action state model storage stores an action state model that is modeled by associating the displacement measurement data with a loaded state of a desired muscle. Moreover, the estimation calculation portion estimates the loaded state by setting the displacement measurement data as an input vector and using the action state model.

In this configuration, the loaded state is estimated by directly using the displacement measurement data, which significantly reduces a processing load while achieving a desired estimation accuracy.

BRIEF DESCRIPTION OF DRAWINGS

FIG. 2 is a table showing an example of a setting of a level of importance according to the first exemplary embodiment.

FIG. 6A shows an example of time variation of signal strength, FIG. 6B shows signal strength distribution, and FIG. 6C shows strength block data.

FIG. 7 is a table showing an example of a setting of a level of importance according to a second exemplary embodiment.

FIG. 8A shows an example of time variation of signal strength, FIG. 8B shows strength block data (an average value), and FIG. 8C is a view showing strength block data (an integrated value).

FIG. 10A and FIG. 10B are tables showing an example of a setting of a level of importance according to the third exemplary embodiment.

FIG. 14A and FIG. 14B are tables showing an example of a setting of a level of importance according to a fourth exemplary embodiment.

DETAILED DESCRIPTION OF THE EXEMPLARY EMBODIMENTS

First Exemplary Embodiment

An action state estimation technology and an action state model generation technology according to a first exemplary embodiment will be described with reference to the drawings.

(Configuration and Processing of Action State Estimation Apparatus)

Figure 1:
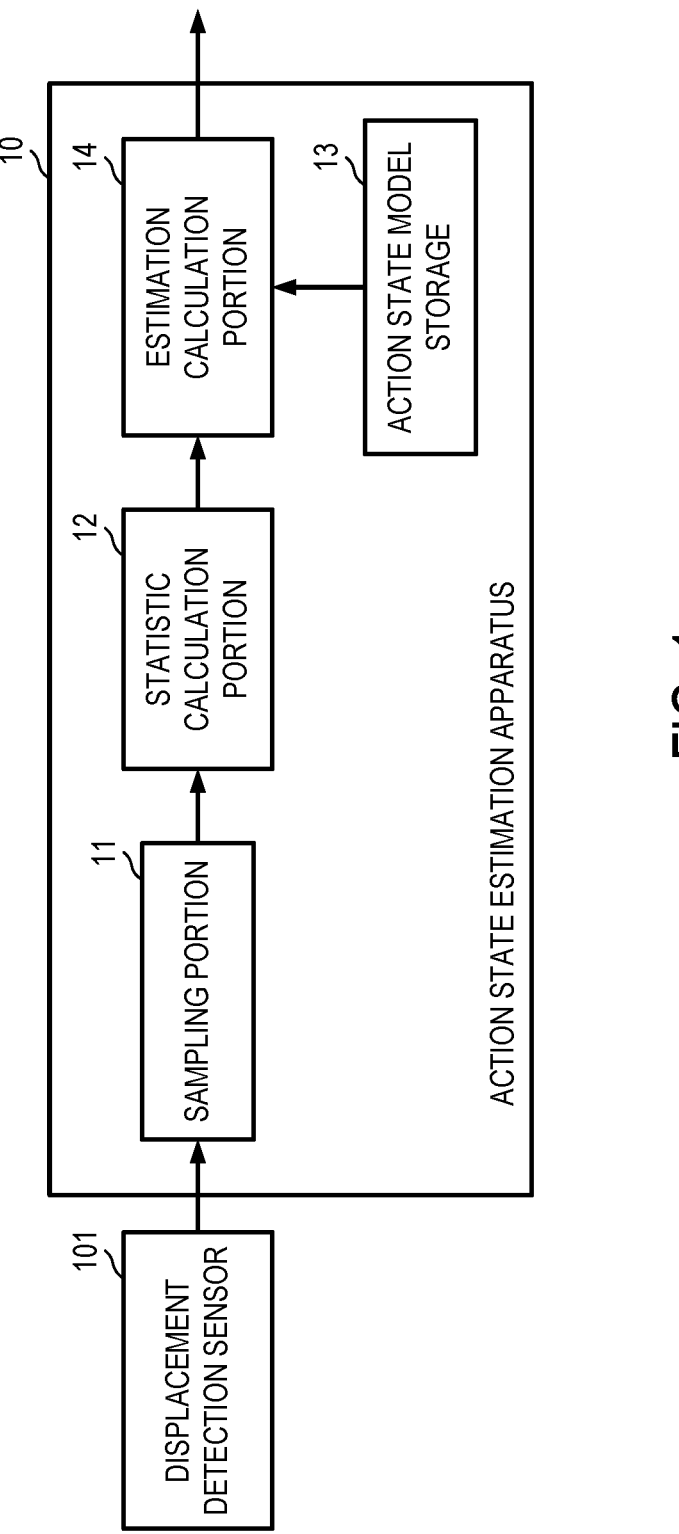
FIG. 1 is a functional block diagram of an action state estimation apparatus according to a first exemplary embodiment.

FIG. 1 is a functional block diagram of an action state estimation apparatus according to the first exemplary embodiment. As shown in FIG. 1, the action state estimation apparatus 10 includes a sampling portion 11, a statistic calculation portion 12, an estimation calculation portion 14, and an action state model storage 13. According to an exemplary aspect, each portion provided to configure the action state estimation apparatus 10 can be implemented by an electronic circuit, an IC, a storage medium storing a program to execute a function of each function portion, and a calculation processing device (such as a CPU) that is configured to execute the program to implement the corresponding portion.

In operation, the sampling portion 11 receives an input of a displacement measurement signal from a displacement detection sensor 101. The sampling portion 11 generates displacement measurement data by sampling the displacement measurement signal by a predetermined sampling frequency (100 Hz, for example). In other words, the sampling portion 11 generates the displacement measurement data without converting the displacement measurement signal into a frequency component. The sampling portion 11 outputs the displacement measurement data to the statistic calculation portion 12.

It is noted that the displacement detection sensor 101 is achieved by a piezoelectric sensor, an acceleration sensor, or the like. The displacement detection sensor 101 does not need to be disposed at a position of a muscle of which the loaded state is estimated, and may be disposed at a position at which a tremor to be produced by the muscle to be estimated can be measured. In addition, the displacement detection sensor 101 may be one sensor disposed at one location or may be two or more sensors disposed at two or more locations. The displacement detection sensor 101 generates and outputs a displacement measurement signal. The displacement measurement signal is a signal obtained by converting displacement on a skin surface due to tremor and deformation into the voltage.

The tremor in the present invention as used herein is an involuntary movement that shows rhythmical muscle activity, for example. In other words, the tremor in the present invention is fine and fast postural tremor seen in normal people, is called a physiological tremor, and is a frequency from 8 Hz to 12 Hz, for example. It is noted that shaking seen in an ill individual such as a Parkinson's patient is a pathologic tremor, is a frequency from 4 Hz to 7 Hz, for example, and is not considered as an object of the tremor in the present invention. The use of a tremor provides the following various types of advantages over myoelectric potential. For example, detection (e.g., measurement) of a tremor can be performed without a direct attachment to a surface (e.g., a skin or the like) of a body, such as a human body, to be detected. The detection of a tremor can detect muscle contraction and expansion. Moreover, the detection of a tremor can detect a variation associated with muscle fatigue.

The statistic calculation portion 12 calculates a statistic from the displacement measurement data. The statistic calculation portion 12 calculates statistics from a plurality of displacement measurement data within a predetermined period (for 1 second, for example).

Types of statistics include, for example, an average value, a maximum value, a minimum value, a median value, a 1% value, a 5% value, a 25% value, a 75% value, a 95% value, a 99% value, a variance value, a skewness value, a kurtosis value, and an integrated value. It is noted that the types of statistics are not limited to these examples, and may be others as long as a value is obtained from time-series displacement measurement data. The statistic calculation portion 12 calculates a plurality of types of statistics out of these values. It is noted that an x % value refers to a value located at x % counted in ascending order from the minimum value, among the plurality of displacement measurement data within a period.

The statistic calculation portion 12 outputs the plurality of types of statistics that have been calculated, to the estimation calculation portion 14.

The action state model storage 13 stores an action state model. The action state model includes a relationship between various types of statistics of displacement measurement data and a loaded state of a muscle to be estimated. The action state model is previously generated by an action state learning apparatus 20 to be described below, for example, and is stored in the action state model storage 13.

The estimation calculation portion 14 estimates the loaded state of a muscle to be estimated by using the action state model stored in the action state model storage 13 and setting a plurality of statistics as an input vector. In such a case, the estimation calculation portion 14 sets a level of importance of the statistics used for estimation, according to the muscle to be estimated. This level of importance is set to the action state model, for example.

FIG. 2 is a table showing an example of a setting of a level of importance according to the first exemplary embodiment. A muscle M1, a muscle M2, a muscle M3, and a muscle M4 show a type of muscle of which the loaded state can be estimated by measured displacement. For example, in a case in which the displacement detection sensor 101 is disposed at a location at which tendons of an ankle are gathered, more specifically, in front of the ankle and in back of the ankle, the muscle M1, the muscle M2, the muscle M3, and the muscle M4 are able to set a soleus muscle, a gastrocnemius muscle, a tibialis anterior muscle, a quadriceps femoris muscle, a hamstring muscle, or the like. In addition, each of the statistics A1 to A15 is set to any of the above various types of statistics (the average value, the maximum value, the minimum value, the median value, the 1% value, the 5% value, the 25% value, the 75% value, the 95% value, the 99% value, the variance value, the skewness value, the kurtosis value, the integrated value, or the like).

For example, in the case of FIG. 2, with respect to the muscle M1, the level of importance to the estimation is set to an order of the statistic A1, the statistic A2, the statistic A8, the statistic A12, and the statistic A7 in order of the first place, the second place, the third place, the fourth place, and the fifth place. In addition, with respect to the muscle M2, the level of importance to the estimation is set to the order of the statistic A3, the statistic A5, the statistic A2, the statistic A14, and the statistic A15 in order of the first place, the second place, the third place, the fourth place, and the fifth place. Hereinafter, with respect to the muscle M3 and the muscle M4 as well, as shown in FIG. 2, the level of importance is set to the statistic.

The estimation calculation portion 14, when setting the muscle to be estimated, estimates a loaded state (e.g., a muscle potential value) of the muscle from the plurality of statistics, by using the level of importance that is set according to the muscle. It is noted that the loaded state of the muscle is not limited to the muscle potential value and may be anything else expressed as a value.

More specifically, for example, the estimation calculation portion 14 calculates an estimation result of the loaded state for each statistic that is estimated from each of the statistics ranked from the first place to the fifth place in the level of importance and the action state model. Then, the estimation calculation portion 14 weights each estimation result according to the level of importance, and calculates an estimation result of a final loaded state by performing addition averaging or the like, for example. It is noted that the number of statistics the estimation calculation portion 14 uses for estimation is not limited to this example. For example, estimation calculation may be performed from the statistics ranked from the first place to the tenth place in the level of importance.

The estimation calculation portion 14, when the number of types of the muscle to be estimated is one, estimates a loaded state by using the statistic and the level of importance according to the muscle. On the other hand, the estimation calculation portion 14, when the number of types of the muscle to be estimated is two or more, sets a statistic and a level of importance for each muscle and estimates a loaded state with respect to each muscle.

With such a configuration, the action state estimation apparatus 10 is configured to estimate the loaded state of a muscle without performing processing to convert measurement data into a frequency component. As a result, the action state estimation apparatus 10 is significantly reduces a processing load while achieving a desired estimation accuracy.

Furthermore, with such a configuration, the action state estimation apparatus 10, for each muscle to be estimated, individually sets the type of statistic used for estimation, and the level of importance. As a result, the action state estimation apparatus 10 is configured to estimate the loaded state of a muscle with higher accuracy.

In addition, with such a configuration, the action state estimation apparatus 10, even when the position of the displacement detection sensor 101 is not at a position of a muscle to be estimated, is configured to estimate the loaded state of the muscle. As a result, the action state estimation apparatus 10 is also configured to estimate the loaded state with respect to a muscle that is not appeared on a body surface or a muscle (e.g., a muscle away from a position in which the displacement detection sensor 101 is disposed) for which the muscle potential is not able to be directly measured. The displacement detection sensor 101 is disposed on an ankle, so that the action state estimation apparatus 10 is configured to estimate the loaded state of a quadriceps femoris muscle, a hamstring muscle (e.g., a biceps femoris muscle, a semimembranosus muscle, a semitendinosus muscle, an adductor magnus muscle), a tibialis anterior muscle, a gastrocnemius muscle, a soleus muscle, and a gluteus maximus muscle. In addition, the action state estimation apparatus 10 is configured to estimate a linked state of a plurality of muscles.

Moreover, an effect due to an error in the position in which the displacement detection sensor 101 is disposed can be significantly reduced. Therefore, the disposition of the displacement detection sensor 101 is facilitated, and an operation for estimation of a loaded state is facilitated.

In addition, with such a configuration, the loaded state of a plurality of muscles can be estimated, using the displacement measurement signal of the displacement detection sensor 101 in common, so that an action state estimation system including a sensor and the action state estimation apparatus can be reduced in size.

Moreover, in such a configuration, the statistic to be used and the level of importance are individually set for each muscle to be estimated. Therefore, the action state estimation apparatus 10 is configured to estimate the loaded state of a plurality of muscles with a high accuracy by using the displacement measurement signal of the displacement detection sensor 101 in common.

In addition, with such a configuration, a loaded state can be estimated not as a class but as a value. In this manner, a loaded state is estimated with a value, so that the action state estimation apparatus 10 is configured to present and manage a more accurate loaded state, and is configured to provide more appropriate notification or the like, to a test subject.

(Action State Estimation Method)

Figure 3:
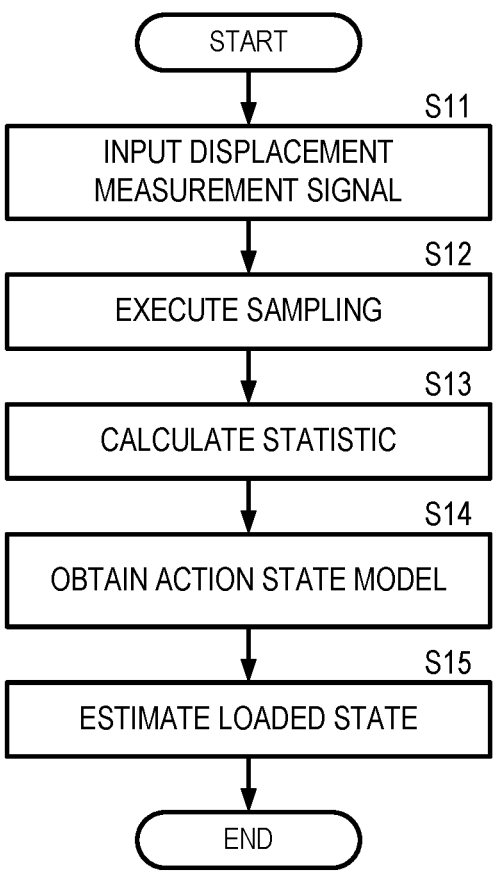
FIG. 3 is a flow chart showing a main process of an action state estimation method according to the first exemplary embodiment.

FIG. 3 is a flow chart showing a main process of an action state estimation method according to the first exemplary embodiment. It is noted that, since the specific content of each processing is described by the above configurations, the following will be schematically described below.

The action state estimation apparatus 10 inputs a displacement measurement signal (S11). The action state estimation apparatus 10 executes sampling to the displacement measurement signal, and generates displacement measurement data (S12). The action state estimation apparatus 10 calculates a statistic from the displacement measurement data (S13).

The action state estimation apparatus 10 obtains an action state model (S14). The action state estimation apparatus 10 estimates a loaded state by using the action state model and setting the statistic as an input vector (S15).

It is noted that the above processing may be programmed and stored in a storage medium or the like, and may be executed by an arithmetic processing apparatus, such as a CPU, according to the exemplary configuration as described herein, for example.

(Configuration and Processing of Action State Learning Apparatus)

Figure 4:
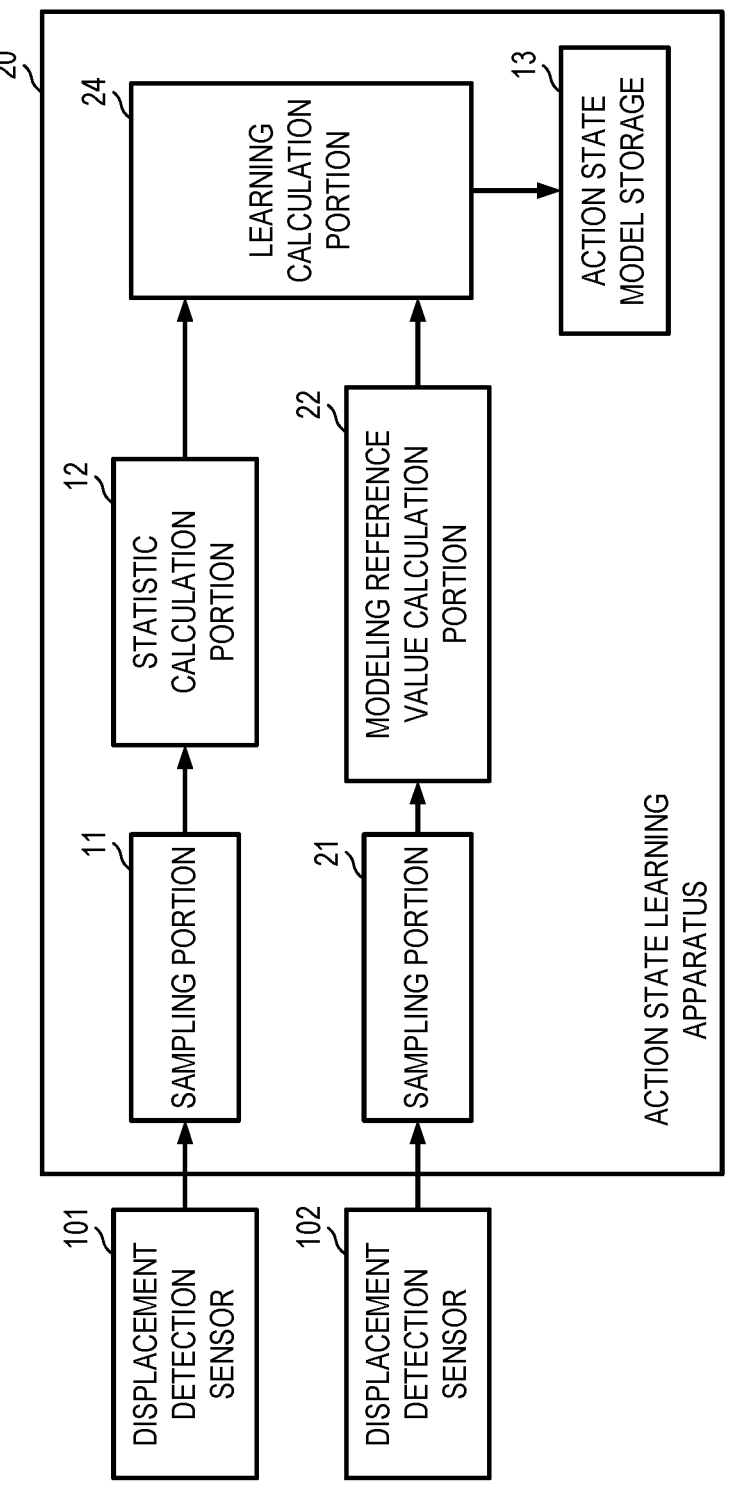
FIG. 4 is a functional block diagram of an action state learning apparatus according to the first exemplary embodiment.

The above action state model is generated, for example, as shown below. FIG. 4 is a functional block diagram of the action state learning apparatus according to the first exemplary embodiment.

As shown in FIG. 4, the action state learning apparatus 20 includes a sampling portion 11, a statistic calculation portion 12, an action state model storage 13, a sampling portion 21, a modeling reference value calculation portion 22, and a learning calculation portion 24. The sampling portion 11, the statistic calculation portion 12, and the action state model storage 13 are as described above, and thus the description will be omitted.

The sampling portion 21 receives an input of a muscle activity measurement signal (e.g., a muscle potential signal) from the muscle activity detection sensor 102. The sampling portion 21 generates muscle activity measurement data by sampling the muscle activity measurement signal by a predetermined sampling frequency (100 Hz, for example). The sampling portion 21 outputs the muscle activity measurement data to the modeling reference value calculation portion 22.

It is noted that the muscle activity detection sensor 102 is a sensor configured for measuring muscle activity, for example, is a myoelectric sensor (e.g., an electromyograph). The muscle activity detection sensor 102 is disposed at a position of a muscle of which the loaded state is to be estimated. More specifically, the muscle activity detection sensor 102 is disposed at a position of a muscle that is a source of muscle activity that produces a tremor to be measured by the muscle activity detection sensor 102. The muscle activity detection sensor 102 detects muscle activity, and generates and outputs a muscle activity measurement signal. The muscle activity detection sensor 102 may be a single sensor disposed with respect to one type of muscles or may be two or more sensors disposed according to a muscle with respect to a plurality of types of muscles.

The modeling reference value calculation portion 22 calculates a modeling reference value from the muscle activity measurement data. For example, the modeling reference value calculation portion 22 calculates an absolute average value of the muscle activity measurement data within a predetermined period as the modeling reference value. The absolute average value refers to an average value of an absolute value of the measurement data.

It is noted that the modeling reference value is not limited to the absolute average value and may use a regressionable value such as, for example, an average value, a maximum value, a minimum value, a median value, a 1% value, a 5% value, a 25% value, a 75% value, a 95% value, a 99% value, a variance value, a skewness value, or a kurtosis value. Furthermore, the modeling reference value can represent a class of a load, such as large, medium, or small, that can be classified from the muscle activity measurement data.

The modeling reference value calculation portion 22 outputs the modeling reference value to the learning calculation portion 24.

The learning calculation portion 24 performs learning by using the statistic and the modeling reference value, and generates an action state model. More specifically, for example, the learning calculation portion 24 performs learning by setting the statistic as an explanatory variable and the modeling reference value as an objective variable and using a gradient boosting method that utilizes a decision tree algorithm. The learning calculation portion 24 repeats the learning, and, when obtaining a predetermined inference accuracy, generates an action state model by using such a result. It is noted that a method of learning is not limited to the gradient boosting method, and may also use a method such as boosting represented by a similar AdaBoost method according to alternative exemplary aspects. In addition, other methods of learning may use an SVM, a GMM, an HMM, a neural network, a learning Bayesian network, or the like. Furthermore, by use of a plurality of learning devices as the learning calculation portion 24, an ensemble method that weights a result of the plurality of learning devices and then performs majority voting may be used.

With the configuration and processing, the action state learning apparatus 20 is configured to properly set the action state model.

(Method of Generating Action State Model)

Figure 5:
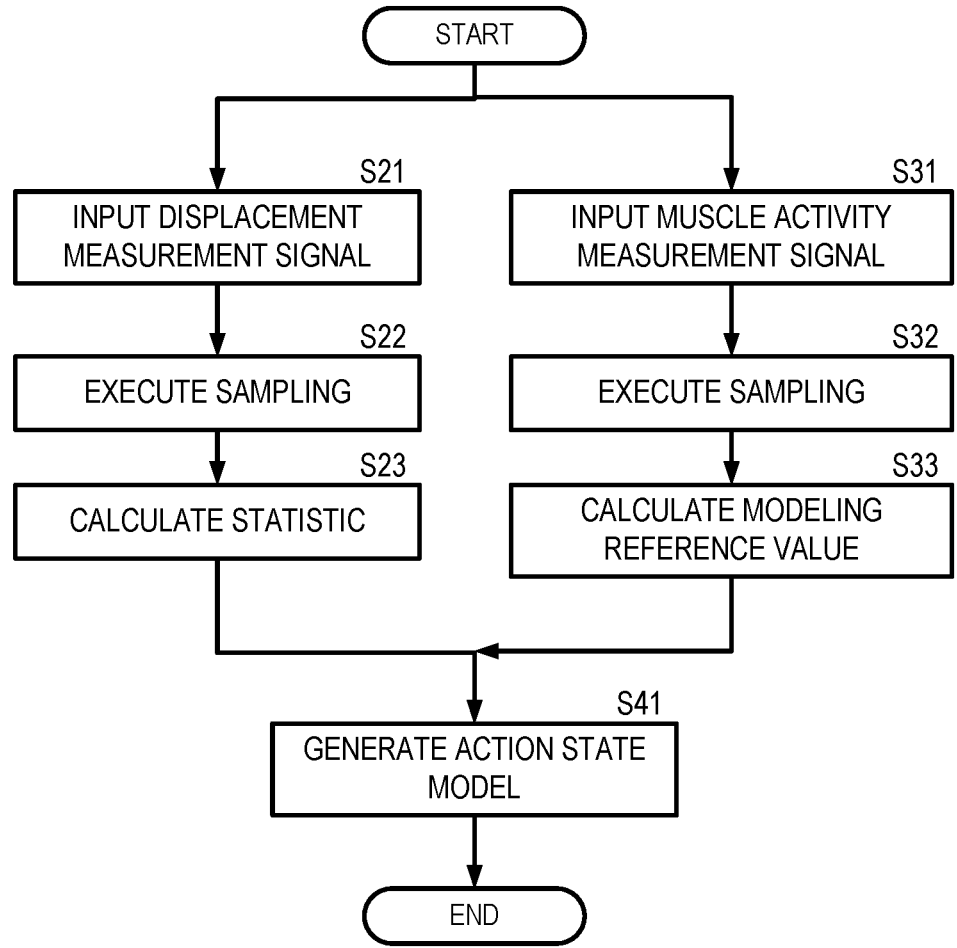
FIG. 5 is a flow chart showing a main process of an action state learning method according to the first exemplary embodiment.

FIG. 5 is a flow chart showing a main process of an action state learning method according to the first exemplary embodiment. It is noted that, since the specific content of each processing is described by the above configurations, the following will be schematically described below.

The action state learning apparatus 20 inputs a displacement measurement signal (S21). The action state learning apparatus 20 executes sampling to the displacement measurement signal, and generates displacement measurement data (S22). The action state learning apparatus 20 calculates a statistic from the displacement measurement data (S23).

The action state learning apparatus 20 inputs a muscle activity measurement signal (S31). The action state learning apparatus 20 executes sampling to the muscle activity measurement signal, and generates muscle activity measurement data (S32). The action state learning apparatus 20 calculates a modeling reference value from the muscle activity measurement data (S33).

The action state learning apparatus 20 executes learning using the statistic and the modeling reference value, and generates an action state model (S41).

It is noted that the above processing may be programmed and stored in a storage medium or the like, and may be executed by an arithmetic processing apparatus, such as a CPU, according to the exemplary configuration as described herein, for example.

In addition, as seen from the configurations of the action state estimation apparatus 10 and the action state learning apparatus 20 according to the present exemplary embodiment, by use of the configuration according to the present exemplary embodiment, during learning, a highly accurate action state model can be generated although it is necessary to use a relatively large-scale muscle potential measurement means such as an electromyograph, whereas, during actual use (e.g., when the action state estimation apparatus 10 is in use), it is unnecessary to use a relatively large-scale muscle potential measurement means such as an electromyograph. In other words, during actual use, with a simple configuration, a loaded state can be estimated (e.g., measured) with a little burden on a test subject.

Second Exemplary Embodiment

An action state estimation technology and an action state model generation technology according to a second exemplary embodiment will be described with reference to the drawings. The action state estimation technology according to the second exemplary embodiment is different in a method of calculating a statistic from the action state estimation technology shown in the first exemplary embodiment. FIG. 6A shows an example of time variation of signal strength, FIG. 6B shows signal strength distribution, and FIG. 6C shows strength block data.

The statistic calculation portion 12 calculates signal strength distribution from displacement measurement data within a predetermined period. The signal strength distribution refers to the displacement measurement data within a predetermined period that are arranged in order of increasing signal strength. For example, the statistic calculation portion 12, as shown in FIG. 6A, when obtaining the signal strength of time t1 to time t100 set by a predetermined sampling period (e.g., a sampling frequency), as shown in FIG. 6B, sets a rank R1 to a rank R100 in order of increasing signal strength and arranges ranks in order from the rank R1 to the rank R100.

The statistic calculation portion 12 generates strength block data from the signal strength distribution, and outputs the strength block data as a statistic. More specifically, the statistic calculation portion 12 sets a strength block (e.g., a signal strength block) for each predetermined number in order of increasing signal strength against the signal strength distribution. The statistic calculation portion 12 calculates an integrated value for each strength block, and generates the strength block data. For example, in the case of FIG. 6C, the statistic calculation portion 12 divides the measurement data into blocks of 10 pieces each. In one example, the statistic calculation portion 12 sets the signal strength from the rank R1 to the rank R10 as a strength block B1, and calculates an integrated value of the signal strength from the rank R1 to the rank R10. The statistic calculation portion 12 performs such processing from the strength block B1 to a strength block B10, and outputs a result as a statistic.

The estimation calculation portion 14 estimates an action state by using the statistic based on the signal strength distribution. In such a case, the estimation calculation portion 14 estimates an action state by using the level of importance.

FIG. 7 is a table showing an example of a setting of the level of importance according to the second exemplary embodiment. As shown in FIG. 7, in the second exemplary embodiment, the level of importance is set for each muscle, to the strength block of the signal strength distribution.

For example, in the case of FIG. 7, with respect to the muscle M1, the level of importance to the estimation is set to an order of the strength block B10, the strength block B9, the strength block B6, the strength block B3, and the strength block B5 in order of the first place, the second place, the third place, the fourth place, and the fifth place. In addition, with respect to the muscle M2, the level of importance to the estimation is set to an order of the strength block B10, the strength block B8, the strength block B9, the strength block B7, and the strength block B1 in order of the first place, the second place, the third place, the fourth place, and the fifth place. Hereinafter, with respect to the muscle M3 and the muscle M4 as well, as shown in FIG. 7, the level of importance is set to the statistic (e.g., the strength block).

The estimation calculation portion 14, when setting a muscle to be estimated, estimates a loaded state of the muscle from a plurality of statistics (e.g., a value of the strength block), by using the level of importance that is set according to the muscle.

With this configuration, the action state estimation apparatus according to the second exemplary embodiment, as with the action state estimation apparatus 10 according to the first exemplary embodiment, is configured to estimate a loaded state of the muscle without performing processing to convert the measurement data into a frequency component. As a result, the action state estimation apparatus according to the second exemplary embodiment significantly reduces a processing load while achieving a necessary estimation accuracy.

It is noted that, in the above description (see FIG. 6A, FIG. 6B, and FIG. 6C), the plurality of measurement data are arranged in order of strength, the plurality of strength blocks are set, and an integrated value is calculated for each of the plurality of strength blocks and used as a statistic. However, in such a case, the integrated value can also be replaced with an average value.

Furthermore, in an aspect to be described below with reference to FIG. 8A, FIG. 8B, and FIG. 8C, a plurality of blocks (time blocks) are set to the plurality of measurement data in a time range, and an average value or an integrated value is calculated for each of the plurality of time blocks and used as a statistic.

In a case of using an average value, the statistic calculation portion 12 divides the plurality of measurement data within time for statistic calculation into a time-series block (e.g., a time block), and calculates an average value for each time block. In a case of using an integrated value, the statistic calculation portion 12 divides the plurality of measurement data within time for statistic calculation into a time-series block (e.g., a time block), and calculates an integrated value for each time block. The statistic calculation portion 12 sets the average value or the integrated value as a value (e.g., a statistic) of the time block.

FIG. 8A shows an example of time variation of signal strength, FIG. 8B shows time block data (e.g., an average value), and FIG. 8C is a view showing time block data (e.g., an integrated value).

For example, when the measurement data as shown in FIG. 8A is obtained, time blocks B1$t$ to B10$t$ arranged over time are set with respect to the signal strength from the time t1 to the time t100. The time block B1$t$ corresponds to time t1 to t10, and the time block B2$t$ corresponds to the time t11 to the time t20. Similarly, the time blocks B3$t$ to B9$t$ are set, and the time block B10$t$ corresponds to the time t91 to the time t100.

In a case of using an average value, for the time block B1$t$, the statistic calculation portion 12 calculates an average value of the signal strength of the time t1 to the time t10, and sets the average value as a statistic of the time block B1$t$. Similarly, the statistic calculation portion 12 calculates an average value of the time blocks B2$t$ to B9$t$, and sets the average value as each statistical value. Then, the statistic calculation portion 12, for the time block B10$t$, calculates an average value of the signal strength of the time t91 to the time t100, and sets the average value as a statistic of the time block B10$t$.

In a case of using an integrated value, for the time block B1$t$, the statistic calculation portion 12 calculates an integrated value of the signal strength of the time t1 to the time t10, and sets the integrated value as a statistic of the time block B1$t$. Similarly, the statistic calculation portion 12 calculates an integrated value of the time blocks B2$t$ to B9$t$, and sets the integrated value as each statistical value. Then, the statistic calculation portion 12, for the time block B10$t$, calculates an integrated value of the signal strength of the time t91 to the time t100, and sets the integrated value as a statistic of the time block B10$t$.

Third Exemplary Embodiment

An action state estimation technology and an action state model generation technology according to a third exemplary embodiment will be described with reference to the drawings.

(Configuration and Processing of Action State Estimation Apparatus)

Figure 9:
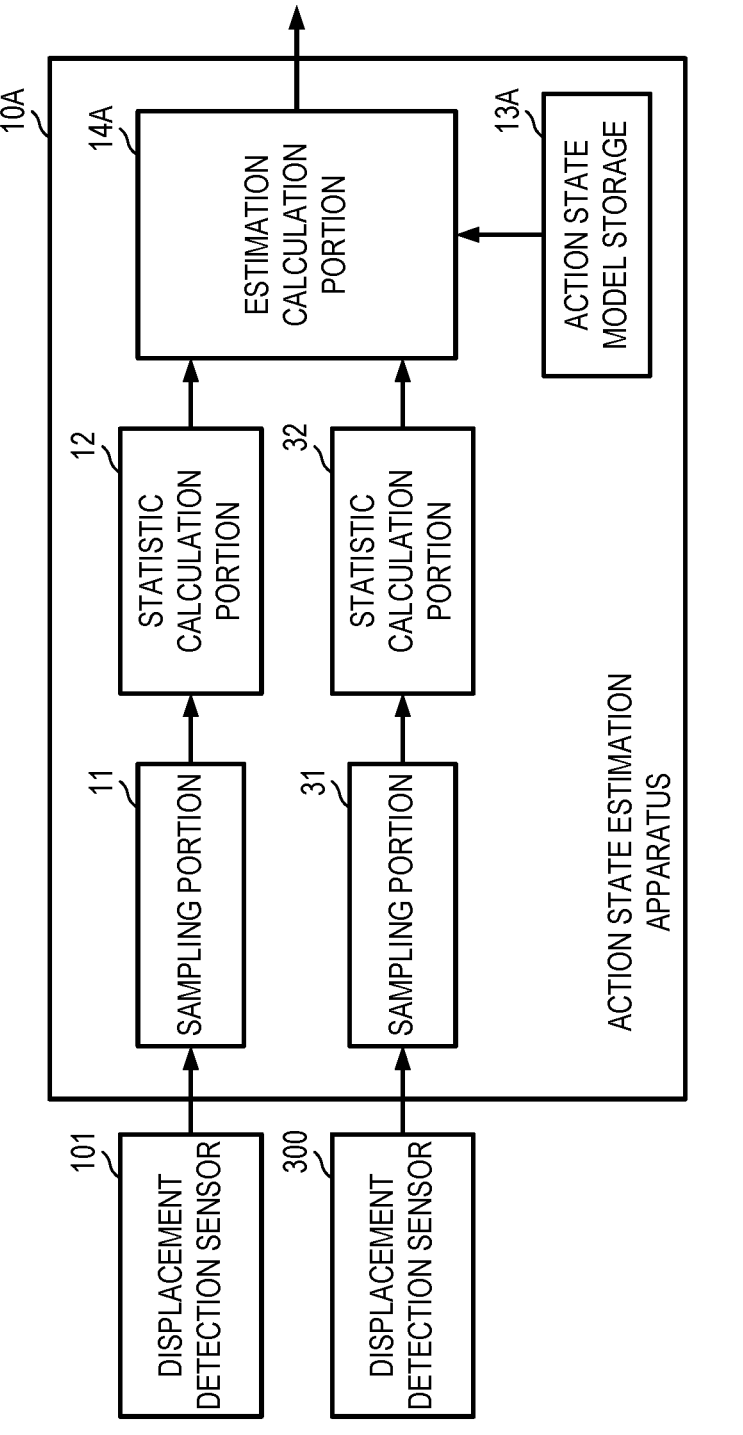
FIG. 9 is a functional block diagram of an action state estimation apparatus according to a third exemplary embodiment.

FIG. 9 is a functional block diagram of an action state estimation apparatus according to the third exemplary embodiment. As shown in FIG. 9, an action state estimation apparatus 10A is different from the action state estimation apparatus 10 according to the first exemplary embodiment in that a sampling portion 31, a statistic calculation portion 32, an action state model storage 13A, and an estimation calculation portion 14A are provided. Other configurations of the action state estimation apparatus 10A are the same as or similar to the configurations of the action state estimation apparatus 10, and a description of the same or similar configurations will be omitted.

The action state estimation apparatus 10A includes a sampling portion 11, a statistic calculation portion 12, an estimation calculation portion 14A, an action state model storage 13A, a sampling portion 31, and a statistic calculation portion 32. Each function portion configuring the action state estimation apparatus 10A can be implemented by an electronic circuit, an IC, a storage medium storing a program to execute a function of each function portion, and a calculation processing device (such as a CPU) that executes the program.

The statistic calculation portion 12 calculates the statistic shown in the first exemplary embodiment as a displacement statistic, and outputs the statistic to the estimation calculation portion 14A.

The sampling portion 31 receives an input of a motion measurement signal from a motion detection sensor 300. The sampling portion 31 generates motion measurement data by sampling the motion measurement signal by a predetermined sampling frequency (100 Hz, for example). In other words, the sampling portion 31 generates the motion measurement data without converting the motion measurement signal into a frequency component. The sampling portion 31 outputs the motion measurement data to the statistic calculation portion 32.

It is noted that the motion detection sensor 300 is used by using an acceleration sensor, an angular velocity sensor, or the like. The motion detection sensor 300 does not need to be disposed at a position of a muscle of which the loaded state is estimated, and may be disposed at a position at which a motion of a test subject to occur by the muscle to be estimated is able to be measured. In addition, the motion detection sensor 300 may be one sensor disposed at one location or may be two or more sensors disposed at two or more locations. The motion detection sensor 300 detects the motion of a test subject, and generates and outputs a motion measurement signal.

The statistic calculation portion 32 calculates a motion statistic from the motion measurement data arranged in time series. The statistic calculation portion 32 calculates a motion statistic from a plurality of motion measurement data within a predetermined period (for 1 second, for example).

Types of motion statistics include, for example, an average value, a maximum value, a minimum value, a median value, a 1% value, a 5% value, a 25% value, a 75% value, a 95% value, a 99% value, a variance value, a skewness value, a kurtosis value, and an integrated value. It is noted that the types of motion statistics are not limited to these examples, and may be others as long as a value is obtained from time-series motion measurement data. The statistic calculation portion 32 calculates a plurality of types of motion statistics out of these values. It is noted that an x % value refers to a value that corresponds to the top x % of the maximum value 100% of the plurality of motion measurement data within a period.

The statistic calculation portion 32 outputs the plurality of types of motion statistics that have been calculated, to the estimation calculation portion 14A.

The action state model storage 13A stores an action state model. The action state model includes a relationship between various types of displacement statistics and various types of motion statistics, and a loaded state of a muscle to be estimated. The action state model is previously generated by an action state learning apparatus 20A to be described below, for example, and is stored (e.g., contained) in the action state model storage 13A.

The estimation calculation portion 14A estimates the loaded state of a muscle to be estimated by using the action state model stored in the action state model storage 13A and setting a displacement statistic and a motion statistic as an input vector. In such a case, the estimation calculation portion 14A sets a level of importance of the displacement statistic and a level of importance of the motion statistic that are used for estimation, according to the muscle to be estimated. The levels of importance are set to the action state model, for example.

FIG. 10A and FIG. 10B are tables showing an example of a setting of the level of importance according to the third exemplary embodiment. FIG. 10A shows the level of importance of the displacement statistic, and FIG. 10B shows the level of importance of the motion statistic. In addition, in FIG. 10A and FIG. 10B, a muscle M1, a muscle M2, a muscle M3, and a muscle M4 show a type of muscles of which the loaded state is able to be estimated by measured displacement. For example, in a case in which the displacement detection sensor 101 is disposed at a place at which tendons of an ankle are gathered, more specifically, in front of the ankle and in back of the ankle, the muscle M1, the muscle M2, the muscle M3, and the muscle M4 are able to set a soleus muscle, a gastrocnemius muscle, a tibialis anterior muscle, a quadriceps femoris muscle, a hamstring muscle, or the like. Each of the displacement statistics Ar1 to Ar15 is set to any one of the above various types of displacement statistics, and each of the motion statistics Aa1 to Aa15 is set to any one of the above various types of motion statistics.

For example, in the case of FIG. 10A, with respect to the muscle M1, the level of importance to the estimation is set to an order of the displacement statistic Ar1, the displacement statistic Ar2, the displacement statistic Ar8, the displacement statistic Ar12, and the displacement statistic Ar7 in order of the first place, the second place, the third place, the fourth place, and the fifth place. In addition, with respect to the muscle M2, the level of importance to the estimation is set to the order of the displacement statistic Ar3, the displacement statistic Ar5, the displacement statistic Ar2, the displacement statistic Ar14, and the displacement statistic Ar15 in order of the first place, the second place, the third place, the fourth place, and the fifth place. Hereinafter, with respect to the muscle M3 and the muscle M4 as well, as shown in FIG. 10A, the level of importance is set to the displacement statistic.

Furthermore, for example, in the case of FIG. 10B, with respect to the muscle M1, the level of importance to the estimation is set to an order of the motion statistic Aa1, the motion statistic Aa2, the motion statistic Aa8, the motion statistic Aa12, and the motion statistic Aa7 in order of the first place, the second place, the third place, the fourth place, and the fifth place. In addition, with respect to the muscle M2, the level of importance to the estimation is set to the order of the motion statistic Aa3, the motion statistic Aa5, the motion statistic Aa2, the motion statistic Aa14, and the motion statistic Aa15 in order of the first place, the second place, the third place, the fourth place, and the fifth place. Hereinafter, with respect to the muscle M3 and the muscle M4 as well, as shown in FIG. 10B, the level of importance is set to the motion statistic.

It is noted that the level of importance of the displacement statistic and the level of importance of the motion statistic with respect to one type of muscles may be set by a common level of importance or may be set individually. For example, in a case in which an index (e.g., a number) of the displacement statistic and an index (e.g., a number) of the motion statistic that are shown in FIG. 10A and FIG. 10B show the same type of a statistic, the level of importance of the displacement statistic and the level of importance of the motion statistic shown in FIG. 10A and FIG. 10B are able to be set by the common level of importance.

On the other hand, when the index (e.g., the number) of the displacement statistic shown in FIG. 10A is set according to the type of the displacement statistic and the index (e.g., the number) of the motion statistic shown in FIG. 10B is set according to the type of the motion statistic, the setting of the level of importance of the displacement statistic and the level of importance of the motion statistic are set individually.

The level of importance of the displacement statistic and the level of importance of the motion statistic are set by the common level of importance, which makes it possible to simplify the setting of the level of importance and also simplify the estimation processing of an action state. On the other hand, the level of importance of the displacement statistic and the level of importance of the motion statistic are set individually, which makes it possible to set more various conditions to estimate an action state and estimate an action state with a further higher accuracy.

The estimation calculation portion 14A, when setting the muscle to be estimated, estimates a loaded state (e.g., a muscle potential value) of the muscle from a plurality of displacement statistics and a plurality of motion statistics, by using the level of importance that is set according to the muscle. It is noted that the loaded state of the muscle is not limited to the muscle potential value and may be anything else expressed as a value.

More specifically, for example, the estimation calculation portion 14A calculates an estimation result of a loaded state from a pair of the displacement statistic of the motion statistic of the same rank in the level of importance and the action state model. The estimation calculation portion 14A calculates the estimation result of a loaded state for each pair of the same rank in the level of importance. Then, the estimation calculation portion 14A weights each estimation result according to the level of importance, and calculates the estimation result of a final loaded state by performing addition averaging or the like, for example.

It is noted that the estimation calculation portion 14A is configured to individually calculate an estimation result of a loaded state from the displacement statistic and the action state model, and an estimation result of a loaded state from the motion statistic and the action state model, and is also configured to calculate an estimation result of a final loaded state from the estimation results. The number of displacement statistics and motion statistics that are used by the estimation calculation portion 14A for estimation is not limited to this example and is configured to be set properly. For example, estimation calculation may be performed from the statistics ranked from the first place to the tenth place in the level of importance.

The estimation calculation portion 14A, when the number of types of the muscle to be estimated is one, estimates a loaded state by using the displacement statistic and the motion statistic and the level of importance according to the muscle. On the other hand, the estimation calculation portion 14A, when the number of types of the muscle to be estimated is two or more, for each muscle, sets the displacement statistic and the motion statistic and the level of importance in each case and estimates a loaded state with respect to each muscle.

With this configuration, the action state estimation apparatus 10A is configured to estimate a loaded state of a muscle by using a detection result of not only displacement including a tremor but a motion such as acceleration, angular velocity, or the like. The detection result of the motion such as sampled acceleration, angular velocity, or the like is strongly influenced by the motion of a test subject, and is highly correlated to muscle activity of the test subject. Then, since the action state estimation apparatus 10A, since estimating an action state from microscopic tremor measurement data and macroscopic motion measurement data, estimates the loaded state of a muscle with a high accuracy.

Furthermore, in this configuration, the displacement measurement data are also sampled measurement data. Therefore, the action state estimation apparatus 10A is configured to significantly reduce lack of information on a tremor associated with frequency conversion, and is also configured to estimate the loaded state of a muscle with higher accuracy.

Furthermore, in such a configuration, the action state estimation apparatus 10A, for each muscle to be estimated, individually sets the type of displacement statistic and the motion statistic that are used for estimation, and the level of importance. As a result, the action state estimation apparatus 10A is configured to estimate the loaded state of a muscle with a much higher accuracy.

In addition, with such a configuration, the action state estimation apparatus 10A, even when the position of the displacement detection sensor 101 and a position of the motion detection sensor 300 are not at a position of a muscle to be estimated, is configured to estimate the loaded state of the muscle. As a result, the action state estimation apparatus 10A is also configured to estimate the loaded state with respect to a muscle that is not appeared on a body surface or a muscle (e.g., a muscle away from a position in which the displacement detection sensor 101 or the motion detection sensor 300 is disposed) for which the muscle potential is not able to be directly measured. The displacement detection sensor 101 and the motion detection sensor 300 are disposed on an ankle, so that the action state estimation apparatus 10A is configured to estimate the loaded state of a quadriceps femoris muscle, a hamstring muscle (e.g., a biceps femoris muscle, a semimembranosus muscle, a semitendinosus muscle, an adductor magnus muscle), a tibialis anterior muscle, a gastrocnemius muscle, a soleus muscle, and a gluteus maximus muscle. In addition, the action state estimation apparatus 10A is configured to estimate a linked state of a plurality of muscles.

Moreover, an effect due to an error in the position in which the displacement detection sensor 101 is disposed can be significantly reduced. Therefore, the disposition of the displacement detection sensor 101 and the motion detection sensor 300 is facilitated, and an operation for estimation of a loaded state is facilitated.

In addition, with such a configuration, the loaded state of a plurality of muscles can be estimated, using the displacement measurement signal of the displacement detection sensor 101 and the motion measurement signal of the motion detection sensor 300 in common, so that an action state estimation system including a sensor and the action state estimation apparatus is reduced in size.

Moreover, in such a configuration, the displacement statistic and the motion statistic that are used and the level of importance are individually set for each muscle to be estimated. Therefore, the action state estimation apparatus 10A is configured to estimate the loaded state of a plurality of muscles with a high accuracy by using a measurement signal of the displacement detection sensor 101 and a measurement signal of the motion detection sensor 300 in common.

In addition, with such a configuration, a loaded state can be estimated not as a class but as a value. In this manner, a loaded state is estimated with a value, so that the action state estimation apparatus 10A is configured to present and manage a more accurate loaded state, and is also configured to provide more appropriate notification or the like, to a test subject.

(Action State Estimation Method)

Figure 11:
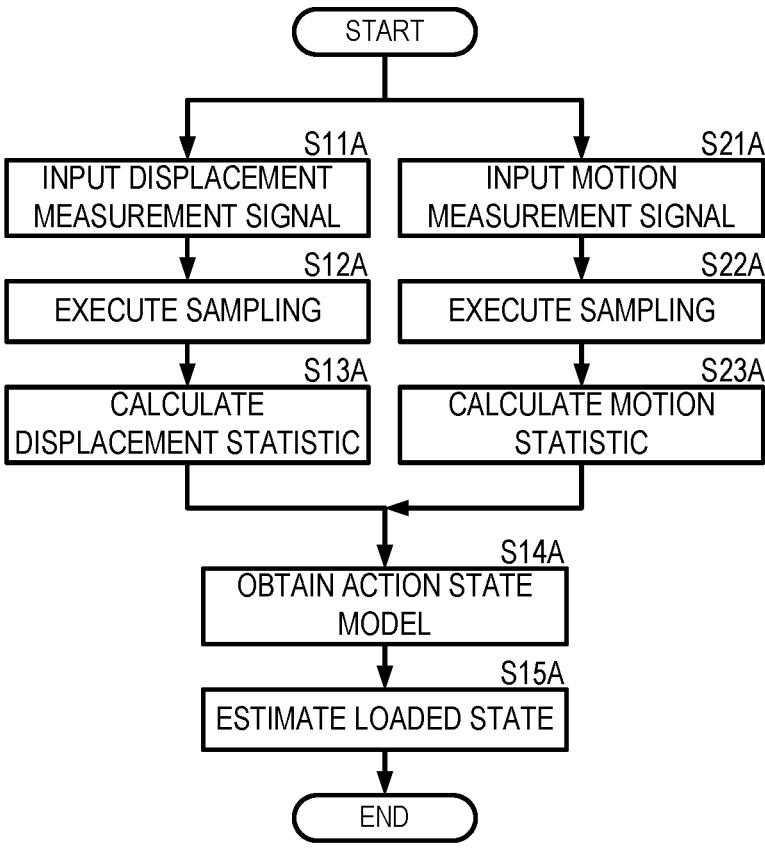
FIG. 11 is a flow chart showing a main process of an action state estimation method according to the third exemplary embodiment.

FIG. 11 is a flow chart showing a main process of an action state estimation method according to the third exemplary embodiment. It is noted that, since the specific content of each processing is described by the above configurations, the following will be schematically described below.

The action state estimation apparatus 10A inputs a displacement measurement signal (S11A). The action state estimation apparatus 10A executes sampling to the displacement measurement signal, and generates displacement measurement data (S12A). The action state estimation apparatus 10A calculates a displacement statistic from the displacement measurement data (S13A).

The action state estimation apparatus 10A inputs a motion measurement signal (S21A). The action state estimation apparatus 10A executes sampling to the motion measurement signal, and generates motion measurement data (S22A). The action state estimation apparatus 10A calculates a motion statistic from the motion measurement data (S23A).

The action state estimation apparatus 10A obtains an action state model (S14A). The action state estimation apparatus 10A estimates a loaded state by using the action state model and setting the displacement statistic and the motion statistic as an input vector (S15A).

It is noted that the above processing may be programmed and stored in a storage medium or the like, and may be executed by an arithmetic processing apparatus such as a CPU, according to the exemplary configuration as described herein, for example.

(Configuration and Processing of Action State Learning Apparatus)

Figure 12:
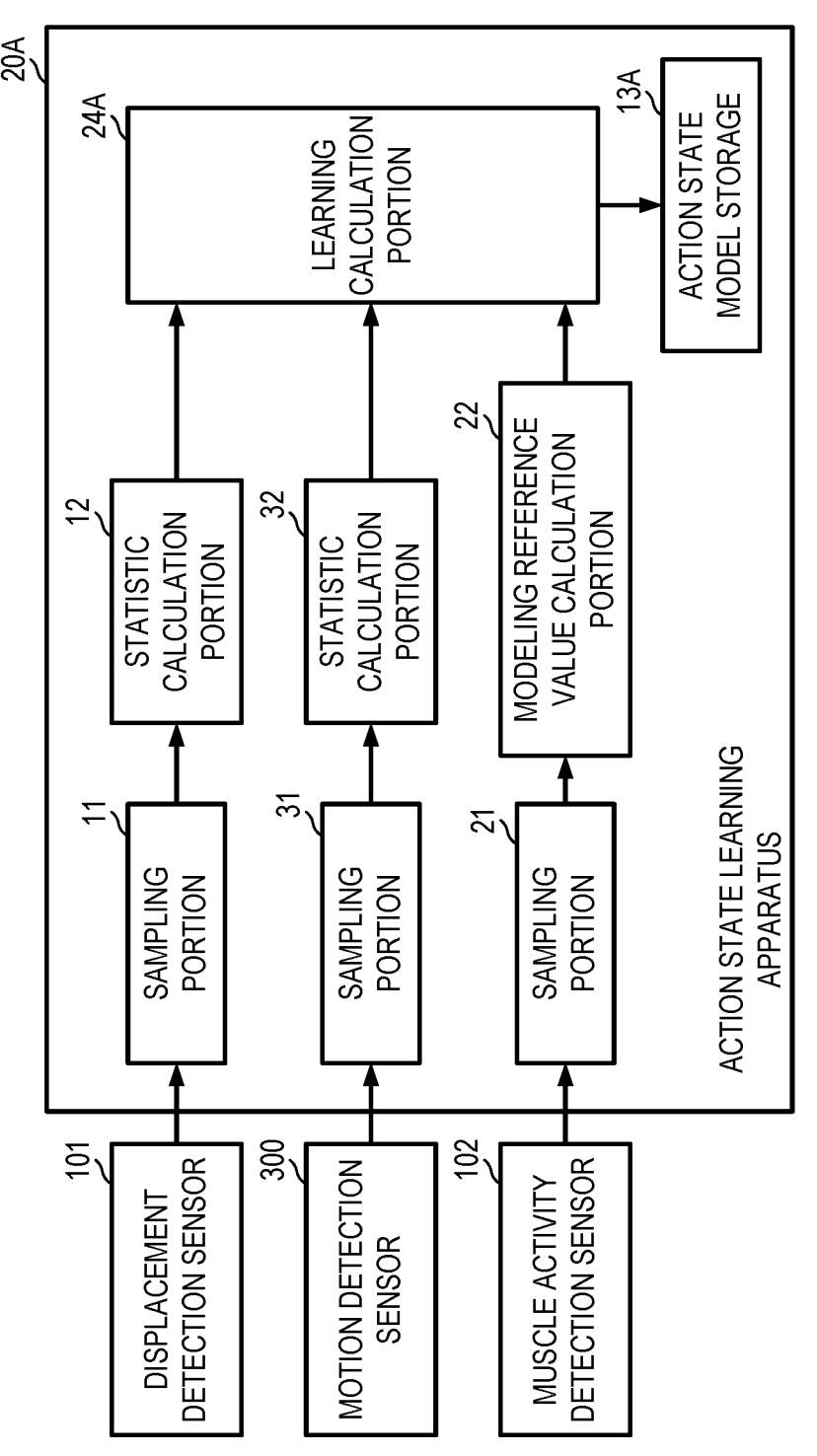
FIG. 12 is a functional block diagram of an action state learning apparatus according to the third exemplary embodiment.

The above action state model is generated, for example, as shown below. FIG. 12 is a functional block diagram of an action state learning apparatus according to the third exemplary embodiment.

As shown in FIG. 12, the action state learning apparatus 20A includes a sampling portion 11, a statistic calculation portion 12, an action state model storage 13A, a sampling portion 21, a modeling reference value calculation portion 22, a learning calculation portion 24A, a sampling portion 31, and a statistic calculation portion 32. The sampling portion 11, the statistic calculation portion 12, the action state model storage 13A, the sampling portion 31, and the statistic calculation portion 32 are as described above, and thus the description will be omitted.

The sampling portion 21 receives an input of a muscle activity measurement signal (e.g., a muscle potential signal) from the muscle activity detection sensor 102. The sampling portion 21 generates muscle activity measurement data by sampling the muscle activity measurement signal by a predetermined sampling frequency (100 Hz, for example). The sampling portion 21 outputs the muscle activity measurement data to the modeling reference value calculation portion 22.

It is noted that the muscle activity detection sensor 102 is a sensor capable of measuring muscle activity, for example, is a myoelectric sensor (e.g., an electromyograph). The muscle activity detection sensor 102 is disposed at a position of a muscle of which the loaded state is to be estimated. More specifically, the muscle activity detection sensor 102 is disposed at a position of a muscle that is a source of muscle activity that produces a tremor to be measured by the muscle activity detection sensor 102. The muscle activity detection sensor 102 detects muscle activity, and generates and outputs a muscle activity measurement signal. The muscle activity detection sensor 102 may be a single sensor disposed with respect to one type of muscles or may be two or more sensors disposed according to a muscle with respect to a plurality of types of muscles.

The modeling reference value calculation portion 22 calculates a modeling reference value from the muscle activity measurement data. For example, the modeling reference value calculation portion 22 calculates an absolute average value of the muscle activity measurement data within a predetermined period as the modeling reference value. The absolute average value refers to an average value of an absolute value of the measurement data.

It is noted that the modeling reference value is not limited to the absolute average value and may use a regressionable value such as, for example, an average value, a maximum value, a minimum value, a median value, a 1% value, a 5% value, a 25% value, a 75% value, a 95% value, a 99% value, a variance value, a skewness value, or a kurtosis value. Furthermore, the modeling reference value can represent a class of a load, such as large, medium, or small, that can be classified from the muscle activity measurement data.

The modeling reference value calculation portion 22 outputs the modeling reference value to the learning calculation portion 24A.

The learning calculation portion 24A performs learning by using the displacement statistic and the motion statistic, and the modeling reference value, and generates an action state model. More specifically, for example, the learning calculation portion 24A performs learning by setting the displacement statistic and the motion statistic as an explanatory variable and the modeling reference value as an objective variable and using a gradient boosting method that utilizes a decision tree algorithm. The learning calculation portion 24A repeats the learning, and, when obtaining a predetermined inference accuracy, generates an action state model by using such a result.

It is noted that a method of learning is not limited to the gradient boosting method, and may also use a method such as boosting represented by a similar AdaBoost method. In addition, other methods of learning may use an SVM, a GMM, an HMM, a neural network, a learning Bayesian network, or the like. Furthermore, by use of a plurality of learning devices as the learning calculation portion 24A, an ensemble method that weights a result of the plurality of learning devices and then performs majority voting may be used.

With the configuration and processing, the action state learning apparatus 20A is configured to properly set the action state model.

(Action State Learning Method)

Figure 13:
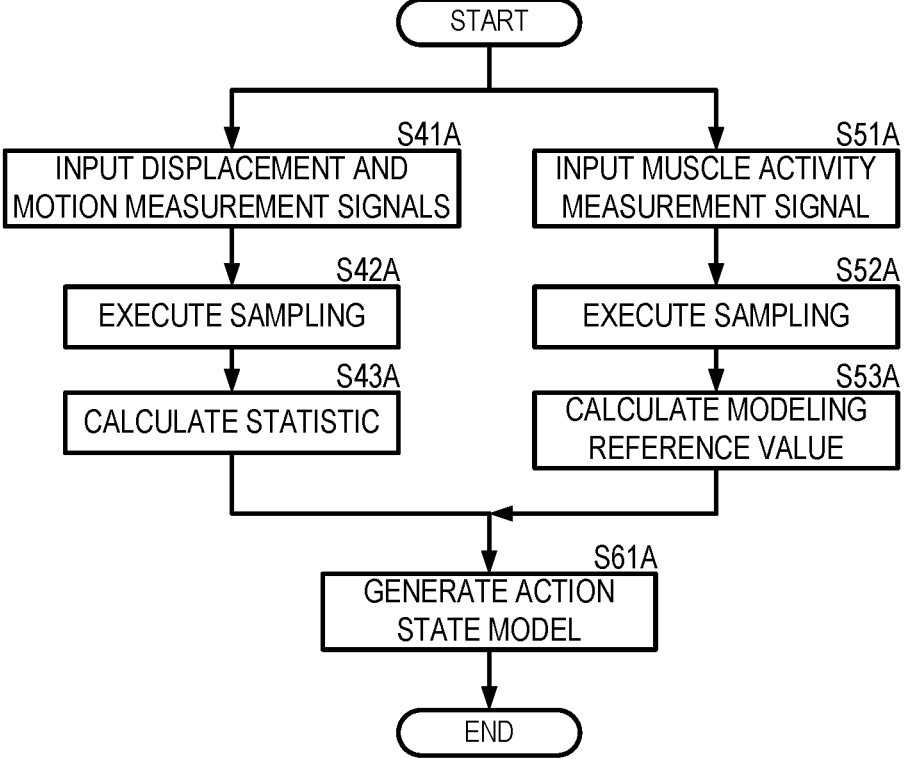
FIG. 13 is a flow chart showing a main process of an action state learning method according to the third exemplary embodiment.

FIG. 13 is a flow chart showing a main process of an action state learning method according to the third exemplary embodiment.

The action state learning apparatus 20A inputs a displacement measurement signal and a motion measurement signal (S41A). The action state learning apparatus 20A executes sampling to the displacement measurement signal, generates displacement measurement data, executes sampling to a motion measurement signal, and generates motion measurement data (S42A). The action state learning apparatus 20A calculates a displacement statistic from the displacement measurement data, and calculates a motion statistic from the motion measurement data (S43A).

The action state learning apparatus 20A inputs a muscle activity measurement signal (S51A). The action state learning apparatus 20A executes sampling to the muscle activity measurement signal, and generates muscle activity measurement data (S52A). The action state learning apparatus 20A calculates a modeling reference value from the muscle activity measurement data (S53A).

The action state learning apparatus 20A executes learning using the displacement statistic and the motion statistic, and the modeling reference value, and generates an action state model (S61A).

It is noted that the above processing may be programmed and stored in a storage medium or the like, and may be executed by an arithmetic processing apparatus, such as a CPU, according to the exemplary configuration as described herein, for example.

Fourth Exemplary Embodiment

An action state estimation technology and an action state model generation technology according to a fourth exemplary embodiment will be described. The action state estimation technology according to the fourth exemplary embodiment is different from the action state estimation technology shown in the third exemplary embodiment in that strength block data of the displacement statistic and the motion statistic is used. A method of generating the strength block data of the motion statistic is the same as or similar to the method of generating the strength block data of the displacement statistic according to the third exemplary embodiment, and thus the description using a specific example will be omitted.

The statistic calculation portion 12 generates strength block data (e.g., displacement strength block data) of displacement measurement data from signal strength distribution of the displacement measurement data, and outputs the strength block data as a displacement statistic. More specifically, the statistic calculation portion 12 sets a strength block (a signal strength block) for each predetermined number in order of increasing signal strength against the signal strength distribution. The statistic calculation portion 12 calculates an integrated value for each strength block, and generates the displacement strength block data.

The statistic calculation portion 32 has the same or similar configuration as the statistic calculation portion 12, and performs the same processing as the statistic calculation portion 12, to the motion measurement data. As a result, the statistic calculation portion 32 calculates and outputs a motion statistic including the strength block data (motion strength block data) of the motion measurement data.

The estimation calculation portion 14A estimates an action state by using the displacement statistic and the motion statistic based on the signal strength distribution. In such a case, the estimation calculation portion 14A estimates an action state by using the level of importance.

FIG. 14A and FIG. 14B are tables showing an example of a setting of the level of importance according to the fourth exemplary embodiment. FIG. 14A shows the level of importance of the displacement statistic, and FIG. 14B shows the level of importance of the motion statistic. As shown in FIG. 14A and FIG. 14B, in the fourth exemplary embodiment, the level of importance is set for each muscle, to the strength block of the signal strength distribution.

The setting of the level of importance shown in FIG. 14A is the same as or similar to the setting of the level of importance shown in FIG. 10A except that the displacement statistic is a value of a strength block. The setting of the level of importance shown in FIG. 14B is the same as or similar to the setting of the level of importance shown in FIG. 10B except that the motion statistic is a value of a strength block. Therefore, the detailed description will be omitted.

The estimation calculation portion 14A, when setting a muscle to be estimated, estimates a loaded state of the muscle from a plurality of displacement statistics (e.g., values of the strength block) and a plurality of motion statistics (e.g., values of the strength block), by using the level of importance that is set according to the muscle.

With this configuration, the action state estimation apparatus according to the fourth exemplary embodiment, as with the action state estimation apparatus 10A according to the third exemplary embodiment, is configured to estimate the loaded state of the muscle with a high accuracy.

Fifth Exemplary Embodiment

An action state estimation technology and an action state model generation technology according to a fifth exemplary embodiment will be described with reference to the drawings. The action state estimation technology according to the fifth exemplary embodiment is different from the action state estimation technology shown in the first exemplary embodiment in that a displacement measurement signal and a muscle activity measurement signal during learning are synchronized. Other methods of the action state estimation technology according to the fifth exemplary embodiment are the same as or similar to the methods of the action state estimation technology according to the first exemplary embodiment, and the description of the same or similar portions will be omitted.

Figure 15:
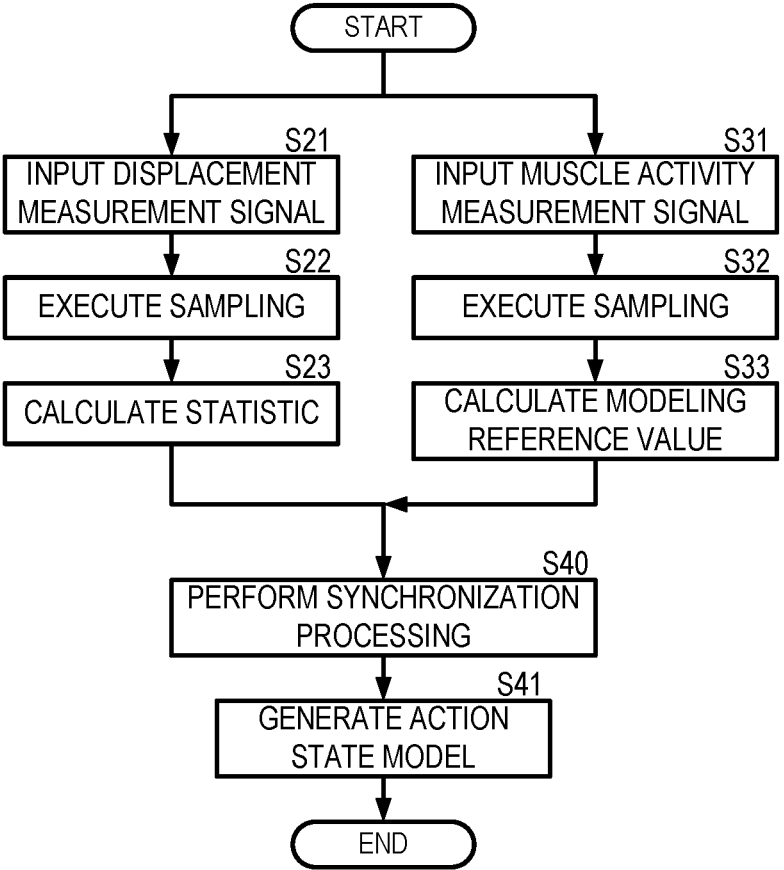
FIG. 15 is a flow chart showing a main process of an action state learning method according to a fifth exemplary embodiment.

FIG. 15 is a flow chart showing a main process of an action state learning method according to the fifth exemplary embodiment. As shown in FIG. 15, the action state learning method according to the fifth exemplary embodiment is different from the action state learning method according to the first exemplary embodiment in that synchronization processing is added. Other processing of the action state learning method according to the fifth exemplary embodiment is the same as or similar to the processing of the action state learning method according to the first exemplary embodiment, and the description of the same or similar processing will be omitted.

Figure 16:
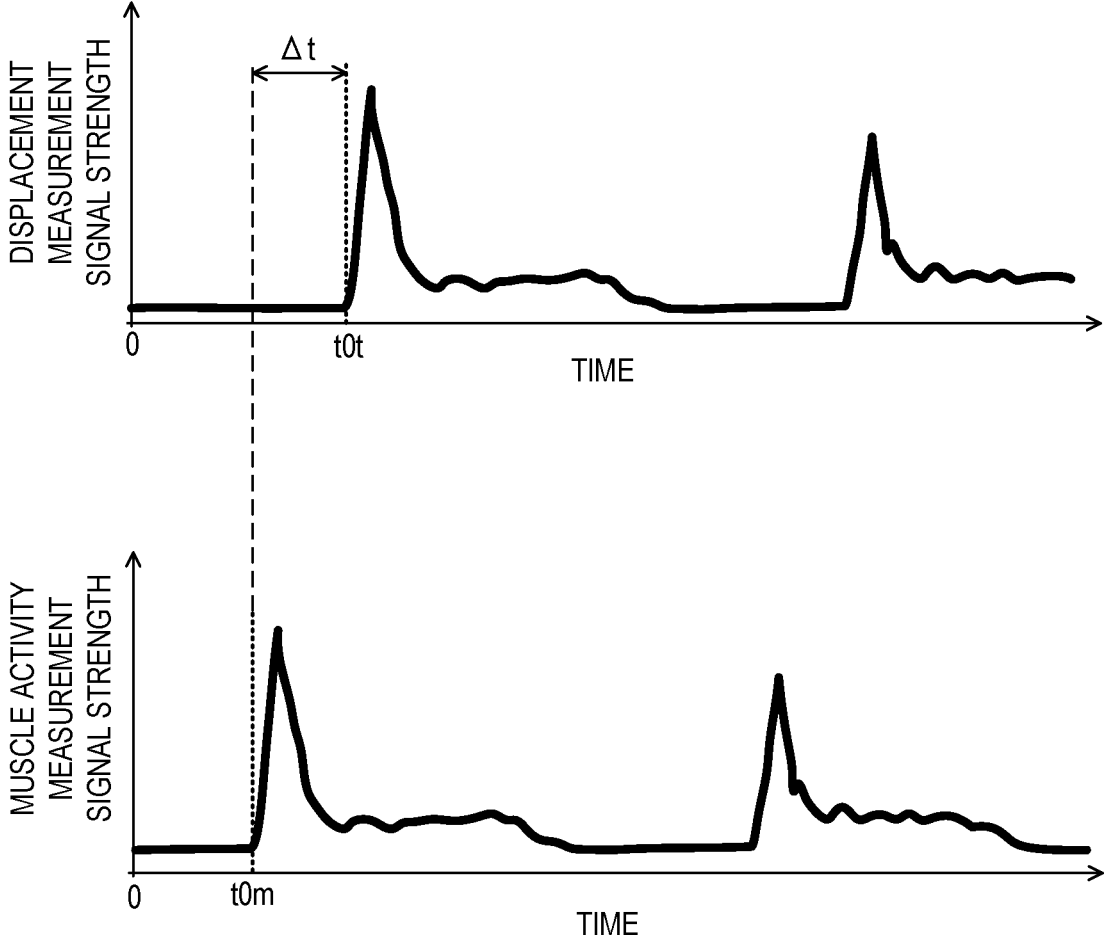
FIG. 16 shows a concept of synchronization.

The action state learning apparatus 20 calculates a statistic and a modeling reference value, and then synchronizes the statistic with the modeling reference value (S40). FIG. 16 shows a concept of synchronization. As shown in FIG. 16, according to a difference in reaction between the displacement detection sensor 101 and the muscle activity detection sensor 102, a time difference Δt occurs between reference time tot of a displacement measurement signal and reference time tom of a muscle activity measurement signal.

Therefore, the learning calculation portion 24 detects the reference time tot of a displacement measurement signal and the reference time tom of a muscle activity measurement signal, and detects a time difference Δt by calculating the difference between the reference time tot and the reference time tom. The learning calculation portion 24 synchronizes the statistic with the modeling reference value by using the time difference Δt.

The learning calculation portion 24 performs learning by using the statistic and the modeling reference value that have been synchronized, and generates an action state model (S41).

By performing such processing, the action state estimation apparatus 10 is configured to estimate the loaded state of a muscle with a higher accuracy.

It is noted that, in a case in which the learning is performed by use of a displacement measurement signal and a motion measurement signal, and a muscle activity measurement signal, the displacement measurement signal and the motion measurement signal may be synchronized with the muscle activity measurement signal to perform the learning.

Sixth Exemplary Embodiment

An action state estimation technology and an action state model generation technology according to a sixth exemplary embodiment will be described with reference to the drawings. The action state estimation technology and the action state model generation technology according to the sixth exemplary embodiment are different from the action state estimation technology and the action state model generation technology that are shown in the first exemplary embodiment in that a feature amount is not used. Other methods of the action state estimation technology and the action state model generation technology according to the sixth exemplary embodiment are the same as or similar to the methods of the action state estimation technology and the action state model generation technology according to the first exemplary embodiment, and the description of the same or similar portions will be omitted.

(Configuration and Processing of Action State Estimation Apparatus)

Figure 17:
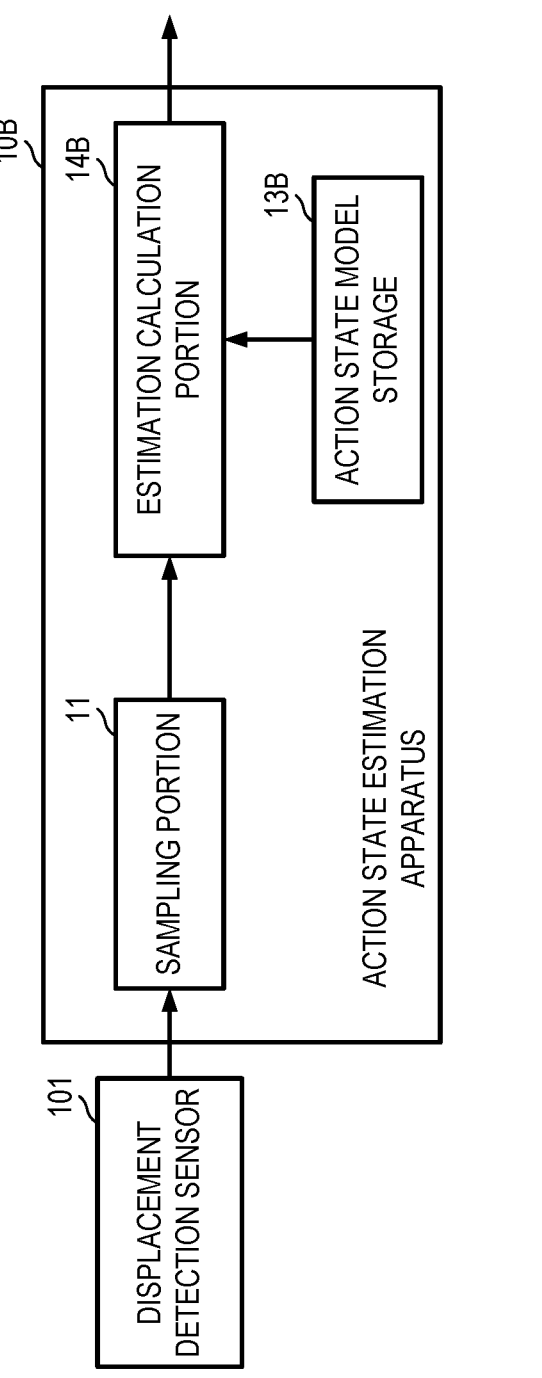
FIG. 17 is a functional block diagram of an action state estimation apparatus according to a sixth exemplary embodiment.

FIG. 17 is a functional block diagram of an action state estimation apparatus according to the sixth exemplary embodiment. As shown in FIG. 17, an action state estimation apparatus 10B includes a sampling portion 11, an action state model storage 13B, and an estimation calculation portion 14B.

The sampling portion 11 outputs displacement measurement data, that is, displacement measurement data (displacement measurement data at a plurality of time points) expressed as a time function, to the estimation calculation portion 14B.

The action state model storage 13B stores an action state model. The action state model includes a relationship between the displacement measurement data and a loaded state of a muscle to be estimated. The action state model is previously generated by an action state learning apparatus 20B to be described below, for example, and is stored in the action state model storage 13B.

The estimation calculation portion 14B estimates the loaded state of a muscle to be estimated by using the action state model stored in the action state model storage 13B and setting the displacement measurement data at the plurality of time points, as an input vector.

In such a manner, the action state estimation apparatus 10B, even when calculating no feature amount, is configured to estimate the loaded state of a muscle to be estimated. As a result, the action state estimation apparatus 10B reduces a processing load.

In such a case, the estimation calculation portion 14B is configured to set a level of importance of the displacement measurement data used for estimation, according to the muscle to be estimated. This level of importance is set to the action state model, for example.

For example, the estimation calculation portion 14B, with reference to measurement start time, makes the level of importance of the displacement measurement data in a predetermined time range after a predetermined time lapse higher than the level of importance of the displacement measurement data in other time ranges. Alternatively, for example, the estimation calculation portion 14B, with reference to measurement start time, groups the displacement measurement data for each predetermined time range, and sets a level of importance for each group.

Figures 18A, 18B:
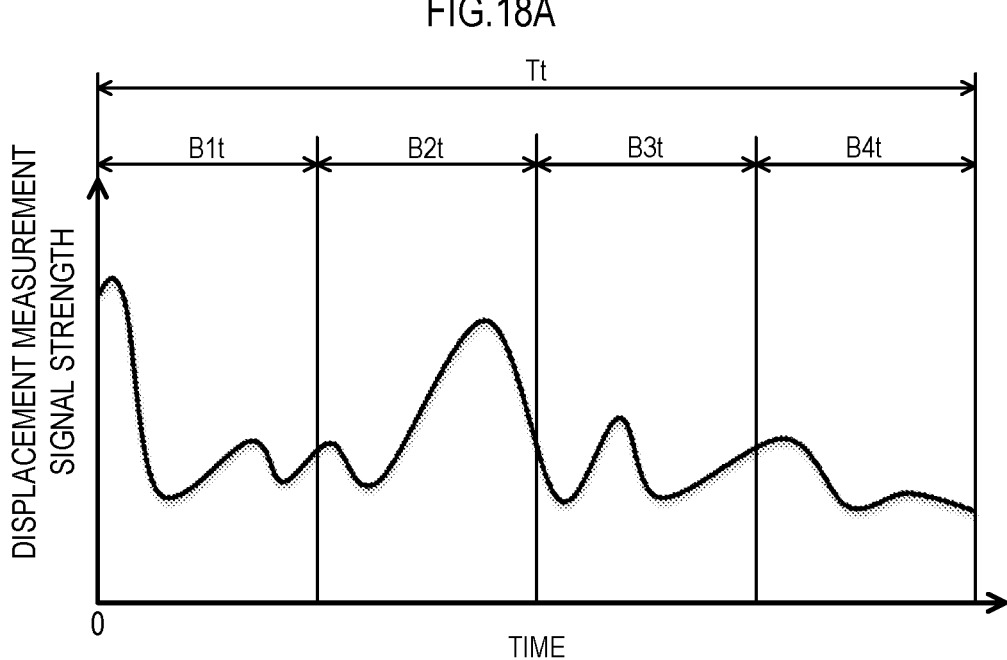
FIG. 18A is a graph showing a waveform for describing the level of importance of a time range, that is, an example of a time range setting.
FIG. 18B shows a table showing an example of a setting of the level of importance by the time range.

FIG. 18A is a graph showing a waveform for describing the level of importance of a time range, that is, an example of a time range setting, and FIG. 18B shows a table showing an example of a setting of the level of importance by the time range. It is noted that, although FIG. 18A and FIG. 18B show a case in which the predetermined time range used for estimation of a loaded state of a muscle is divided into four time ranges, the number of divisions is not limited to this example.

As shown in FIG. 18A, the estimation calculation portion 14B divides a predetermined time range Tt used for estimation of a loaded state of a muscle into a plurality of time ranges B1t, B2t, B3t, and B4t. The estimation calculation portion 14B assigns a plurality of displacement measurement data in the predetermined time range Tt to the plurality of time ranges B1t, B2t, B3t, and B4t according to each measurement time (e.g., obtained time).

As shown in FIG. 18B, the estimation calculation portion 14B stores the level of importance of the plurality of time ranges B1t, B2t, B3t, and B4t with respect to the loaded state of a muscle to be estimated. For example, in a case of the muscle M1 in FIG. 18B, the level of importance of the time ranges B1t and B4t is set to High, and the level of importance of the time ranges B2t and B3t is set to Low. In addition, in a case of the muscle M2 in FIG. 18B, the level of importance of the time ranges B2t and B3t is set to High, and the level of importance of the time ranges B1t and B4t is set to Low.

The level of importance is set by a positional relationship between the muscle to be estimated and the displacement detection sensor 101, for example.

As a specific example, when a distance between the muscle to be estimated and the displacement detection sensor 101 is small, that is, when the displacement detection sensor 101 is disposed in the vicinity of the muscle to be estimated, the effect of the displacement measurement data in first and last time ranges (e.g., a terminal time range) in a predetermined time range to be measured on an estimation result is relatively large, and the effect of the displacement measurement data in a middle time range on an estimation result is relatively small.

Therefore, in the above example, as a case in which the distance between the muscle M1 and the displacement measurement sensor 101 is small, with respect to the muscle M1, the level of importance of the time ranges B1t and B4t corresponding to the first and last time ranges is made high, and the level of importance of the time ranges B2t and B3t corresponding to the middle time range is made low.

In contrast, when a distance between the muscle to be estimated and the displacement detection sensor 101 is large, that is, when the displacement detection sensor 101 is disposed away from the muscle to be estimated, the effect of the displacement measurement data in first and last time ranges (a terminal time range) in a predetermined time range to be measured on an estimation result is relatively small, and the effect of the displacement measurement data in a middle time range on an estimation result is relatively large.

Therefore, in the above example, as a case in which the distance between the muscle M2 and the displacement measurement sensor 101 is large, with respect to the muscle M2, the level of importance of the time ranges B1t and B4t corresponding to the first and last time ranges is made low, and the level of importance of the time ranges B2*t* and B3*t* corresponding to the middle time range is made high.

In such a manner, by setting a level of importance with respect to a time range, the action state estimation apparatus 10B is configured to estimate the loaded state of a muscle to be estimated, with a better accuracy.

It is noted that it is also possible to avoid using the time range of which the level of importance is set to low, for estimation. As a result, the action state estimation apparatus 10B reduces the processing load to perform estimation.

(Action State Estimation Method)

Figure 19:
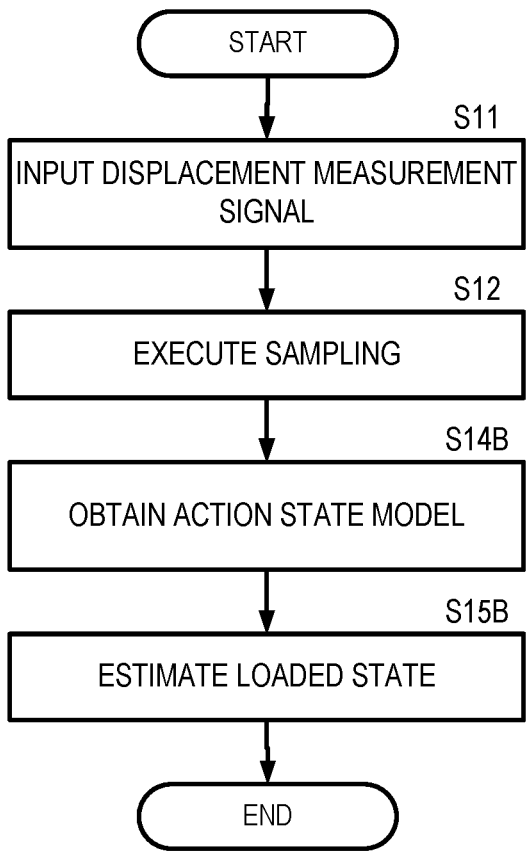
FIG. 19 is a flow chart showing a main process of an action state estimation method according to the sixth exemplary embodiment.

FIG. 19 is a flow chart showing a main process of an action state estimation method according to the sixth exemplary embodiment.

The action state estimation apparatus 10B inputs a displacement measurement signal (S11). The action state estimation apparatus 10B executes sampling to the displacement measurement signal, and generates displacement measurement data (S12).

The action state estimation apparatus 10B obtains an action state model by use of the displacement measurement data (S14B). The action state estimation apparatus 10 estimates a loaded state by using the action state model and setting the displacement measurement data as an input vector (S15B).

It is noted that the above processing may be programmed and stored in a storage medium or the like, and may be executed by an arithmetic processing apparatus, such as a CPU, according to the exemplary configuration as described herein, for example.

(Configuration and Processing of Action State Learning Apparatus)

The above action state model is generated, for example, as shown below.

Figure 20:
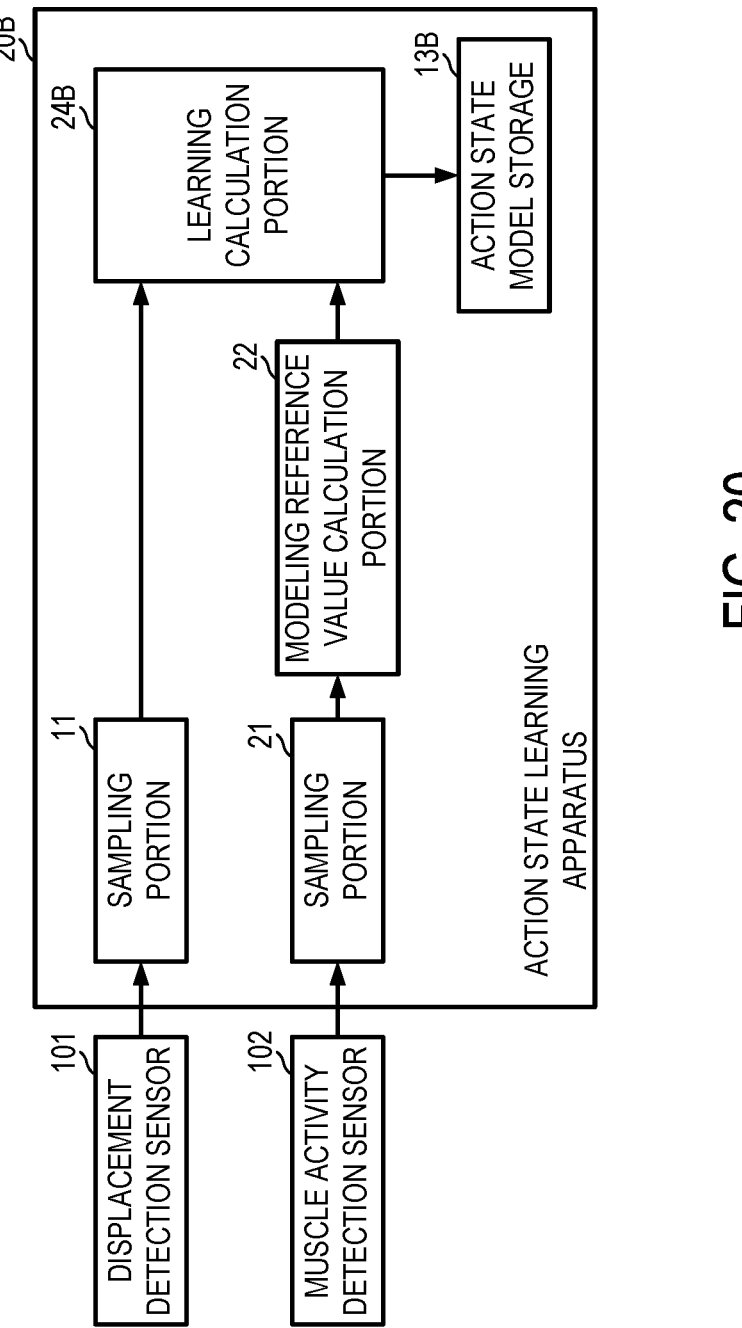
FIG. 20 is a functional block diagram of an action state learning apparatus according to the sixth exemplary embodiment.

FIG. 20 is a functional block diagram of the action state learning apparatus according to the sixth exemplary embodiment.

As shown in FIG. 20, the action state learning apparatus 20B includes a sampling portion 11, an action state model storage 13B, a sampling portion 21, a modeling reference value calculation portion 22, and a learning calculation portion 24B. The sampling portion 11, the sampling portion 21, and the modeling reference value calculation portion 22 are the same as or similar to the portions of the action state learning apparatus 20 according to the first exemplary embodiment, and the description will be omitted.

The learning calculation portion 24B performs learning by using the displacement measurement data and the modeling reference value, and generates an action state model. More specifically, for example, the learning calculation portion 24B performs learning by setting the displacement measurement data as an explanatory variable and the modeling reference value as an objective variable and using a gradient boosting method that utilizes a decision tree algorithm. It is noted that a method of learning is not limited to the gradient boosting method and may use the above various methods.

The learning calculation portion 24B repeats the learning, and, when obtaining a predetermined inference accuracy, generates an action state model by using such a result. The learning calculation portion 24B stores a generated action state model in the action state model storage 13B.

With the configuration and processing, the action state learning apparatus 20B is configured to properly set the action state model without using the feature amount.

In such a case, synchronization processing as shown in the fifth exemplary embodiment is configured to significantly reduce an adverse effect on generation of the action state model by the time difference between the displacement measurement data and the muscle activity measurement data. Therefore, the action state learning apparatus 20B can more properly set the action state model.

(Method of Generating Action State Model)

Figure 21:
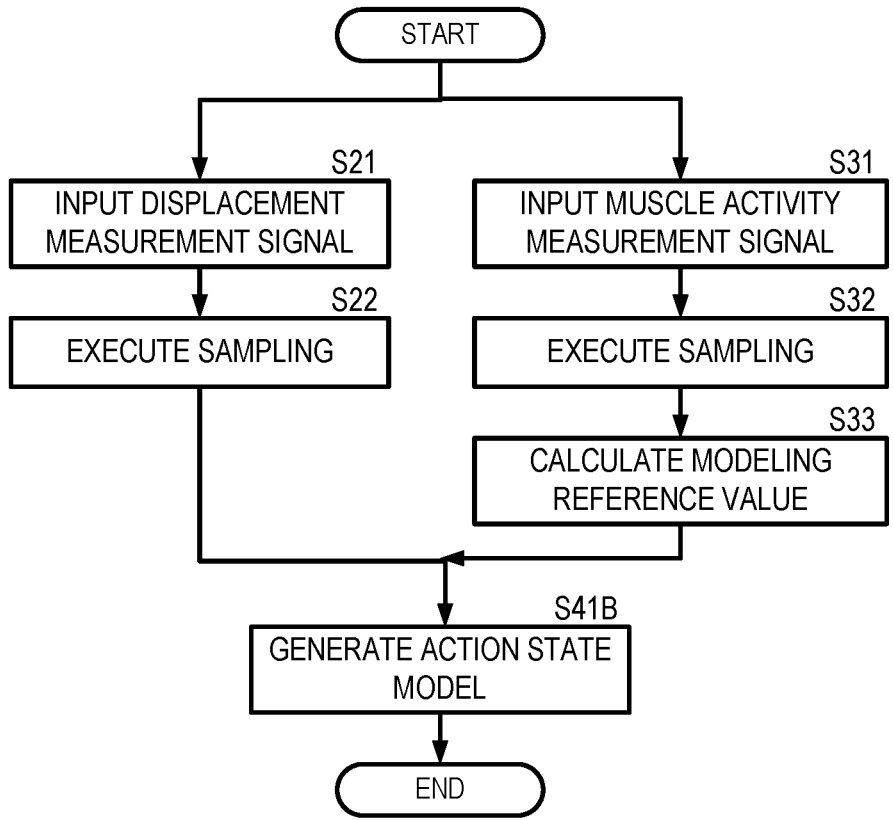
FIG. 21 is a flow chart showing a main process of an action state learning method according to the sixth exemplary embodiment.

FIG. 21 is a flow chart showing a main process of an action state learning method according to the sixth exemplary embodiment.

The action state learning apparatus 20B inputs a displacement measurement signal (S21). The action state learning apparatus 20B executes sampling to the displacement measurement signal, and generates displacement measurement data (S22).

The action state learning apparatus 20B inputs a muscle activity measurement signal (S31). The action state learning apparatus 20B executes sampling to the muscle activity measurement signal, and generates muscle activity measurement data (S32). The action state learning apparatus 20B calculates a modeling reference value from the muscle activity measurement data (S33).

The action state learning apparatus 20B executes learning using the displacement measurement data and the modeling reference value, and generates an action state model (S41B).

It is noted that the above processing may be programmed and stored in a storage medium or the like, and may be executed by an arithmetic processing apparatus, such as a CPU, according to the exemplary configuration as described herein, for example.

Seventh Exemplary Embodiment

An action state estimation technology and an action state model generation technology according to a seventh exemplary embodiment will be described with reference to the drawings.

(Configuration and Processing of Action State Estimation Apparatus)

Figure 22:
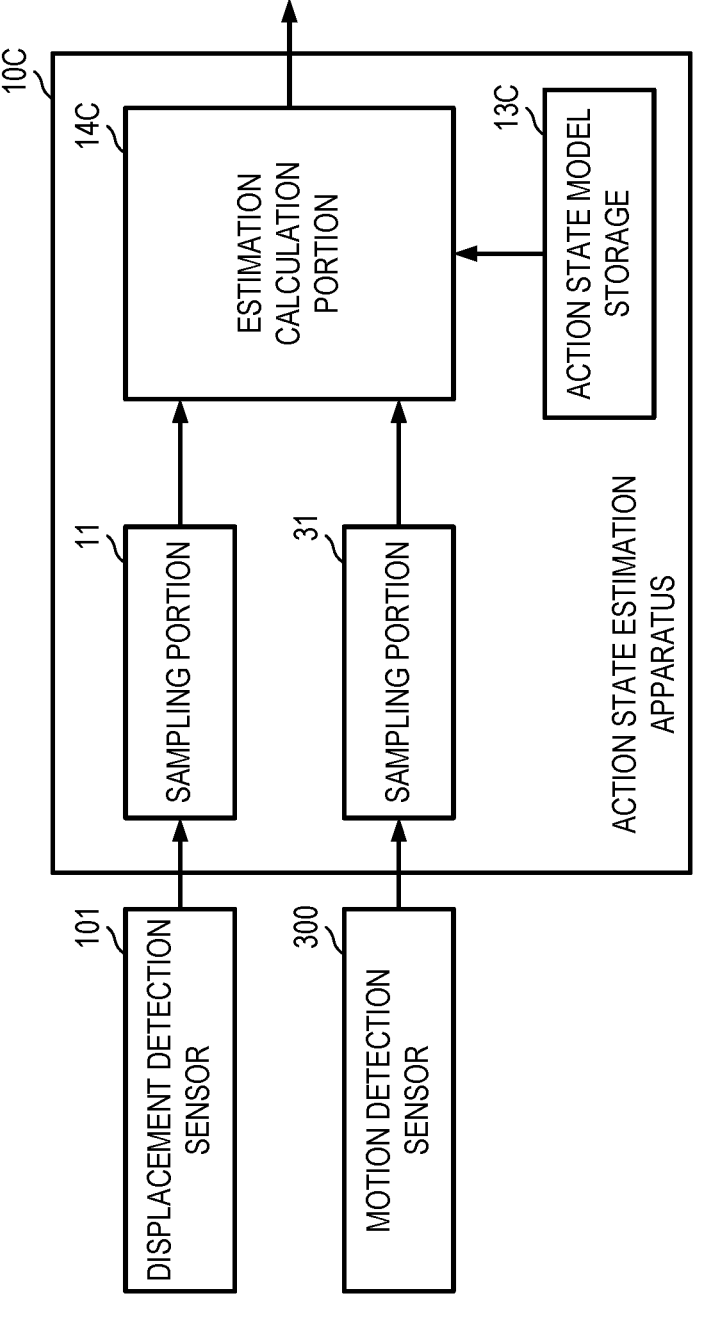
FIG. 22 is a functional block diagram of an action state estimation apparatus according to a seventh exemplary embodiment.

FIG. 22 is a functional block diagram of an action state estimation apparatus according to the seventh exemplary embodiment. As shown in FIG. 22, an action state estimation apparatus 10C is different from the action state estimation apparatus 10A according to the third exemplary embodiment in that a statistic calculation portion is not provided and in that an action state model storage 13C and an estimation calculation portion 14C are provided. Other configurations of the action state estimation apparatus 10C are the same as or similar to the configurations of the action state estimation apparatus 10A, and a description of the same or similar configurations will be omitted.

The action state estimation apparatus 10C includes a sampling portion 11, an estimation calculation portion 14C, an action state model storage 13C, and a sampling portion 31.

The sampling portion 31 outputs calculated motion measurement data to the estimation calculation portion 14C. In such a case, the sampling portion 31 obtains the motion measurement data by an orthogonal triaxial component or a composite value obtained by combining orthogonal triaxial components. The use of such motion measurement data is able to set an input vector configured for estimating a loaded state of a muscle to be estimated with a better accuracy. It is to be noted that both the orthogonal triaxial component and the composite value may be used.

The action state model storage 13C stores an action state model. The action state model includes a relationship between the displacement measurement data and the motion measurement data, and the loaded state of a muscle to be estimated. The action state model is previously generated by an action state learning apparatus 20C to be described below, for example, and is stored (e.g., contained) in the action state model storage 13C.

The estimation calculation portion 14C estimates the loaded state of a muscle to be estimated by using the action state model stored in the action state model storage 13C and setting the displacement measurement data and the motion measurement data, as an input vector. In such a case, the estimation calculation portion 14C is configured to set a level of importance of the displacement measurement data and a level of importance of the motion measurement data that are used for estimation. This level of importance is set to the action state model, for example.

For example, the estimation calculation portion 14C, with reference to measurement start time, makes the level of importance of the displacement measurement data in a predetermined time range after a predetermined time lapse higher than the level of importance of the displacement measurement data in other time ranges. Alternatively, for example, the estimation calculation portion 14C, with reference to measurement start time, groups the displacement measurement data for each predetermined time range, and sets a level of importance for each group. For the motion measurement data, a level of importance can be set in the same manner as for displacement measurement data.

In such a manner, the action state estimation apparatus 10C, even when calculating no feature amount with respect to a plurality of types of measurement data (displacement measurement data and motion measurement data), is configured to estimate the loaded state of a muscle to be estimated.

(Action State Estimation Method)

Figure 23:
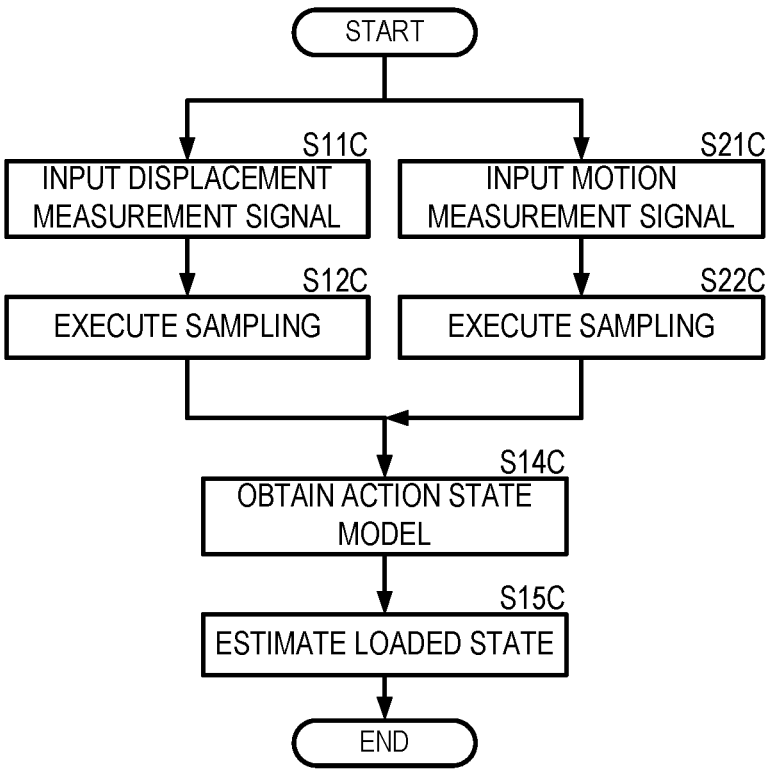
FIG. 23 is a flow chart showing a main process of an action state estimation method according to the seventh exemplary embodiment.

FIG. 23 is a flow chart showing a main process of an action state estimation method according to the seventh exemplary embodiment.

The action state estimation apparatus 10C inputs a displacement measurement signal (S11C). The action state estimation apparatus 10C executes sampling to the displacement measurement signal, and generates displacement measurement data (S12C).

The action state estimation apparatus 10C inputs a motion measurement signal (S21C). The action state estimation apparatus 10C executes sampling to the motion measurement signal, and generates motion measurement data (S22C).

The action state estimation apparatus 10C obtains an action state model (S14C). The action state estimation apparatus 10C estimates a loaded state by using the action state model and setting the displacement measurement data and the motion measurement data as an input vector (S15C).

It is noted that the above processing may be programmed and stored in a storage medium or the like, and may be executed by an arithmetic processing apparatus, such as a CPU, according to the exemplary configuration as described herein, for example.

(Configuration and Processing of Action State Learning Apparatus)

Figure 24:
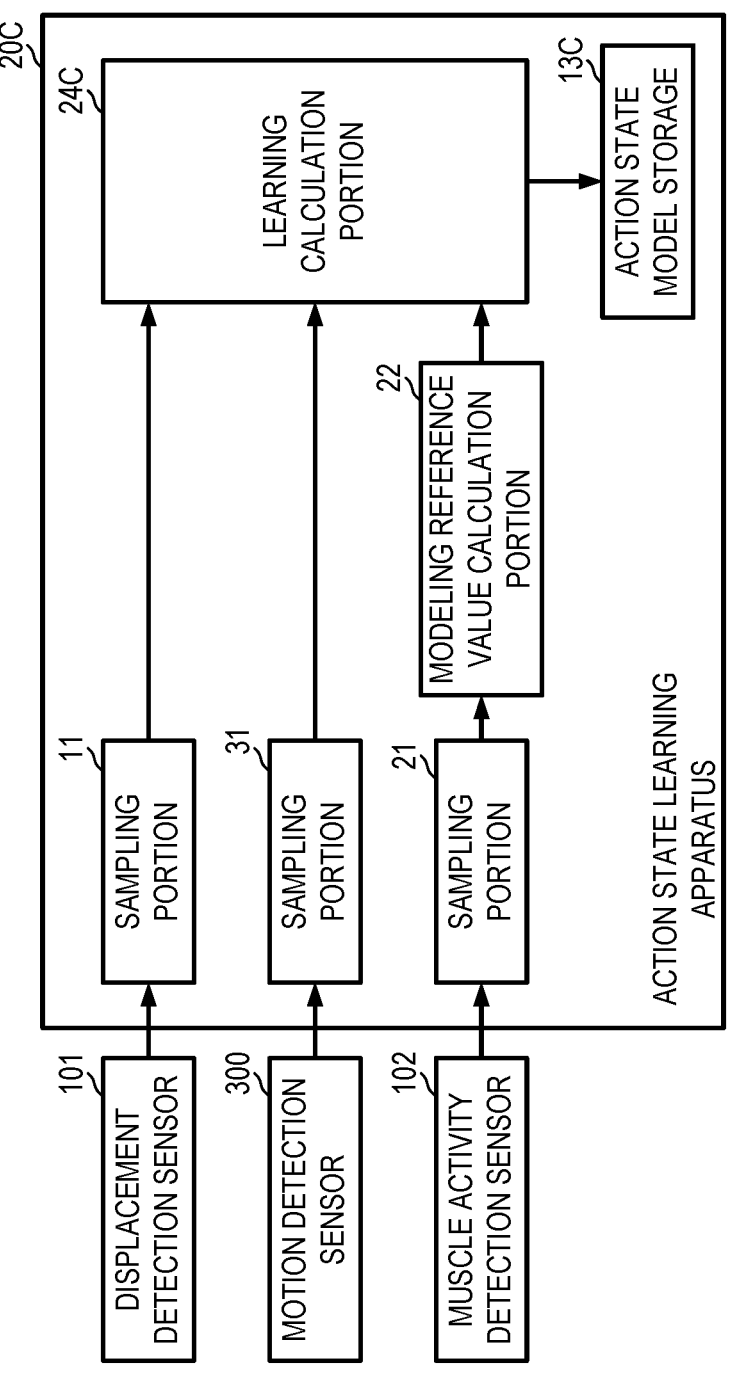
FIG. 24 is a functional block diagram of an action state learning apparatus according to the seventh exemplary embodiment.

The above action state model is generated, for example, as shown below. FIG. 24 is a functional block diagram of the action state learning apparatus according to the seventh exemplary embodiment.

As shown in FIG. 24, the action state learning apparatus 20C includes a sampling portion 11, an action state model storage 13C, a sampling portion 21, a modeling reference value calculation portion 22, a learning calculation portion 24C, and a sampling portion 31.

The learning calculation portion 24C performs learning by using the displacement measurement data and the motion measurement data, and the modeling reference value, and generates an action state model. More specifically, for example, the learning calculation portion 24C performs learning by setting the displacement measurement data and the motion measurement data as an explanatory variable and the modeling reference value as an objective variable and using a gradient boosting method that utilizes a decision tree algorithm. The learning calculation portion 24C repeats the learning, and, when obtaining a predetermined inference accuracy, generates an action state model by using such a result. It is noted that a method of learning is not limited to the gradient boosting method and may use the above various methods.

The learning calculation portion 24C repeats the learning, and, when obtaining a predetermined inference accuracy, generates an action state model by using such a result. The learning calculation portion 24C stores a generated action state model in the action state model storage 13C.

With the configuration and processing, the action state learning apparatus 20C can properly set the action state model.

(Action State Learning Method)

Figure 25:
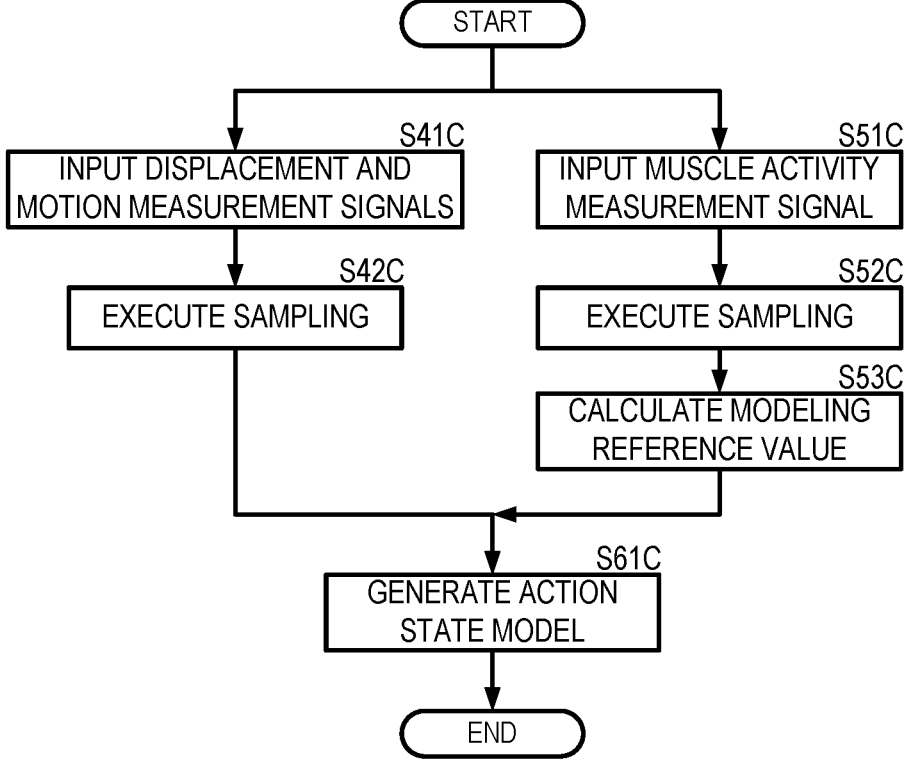
FIG. 25 is a flow chart showing a main process of an action state learning method according to the seventh exemplary embodiment.

FIG. 25 is a flow chart showing a main process of an action state learning method according to the seventh exemplary embodiment.

The action state learning apparatus 20C inputs a displacement measurement signal and a motion measurement signal (S41C). The action state learning apparatus 20C executes sampling to the displacement measurement signal, generates displacement measurement data, executes sampling to a motion measurement signal, and generates motion measurement data (S42C).

The action state learning apparatus 20C inputs a muscle activity measurement signal (S51C). The action state learning apparatus 20C executes sampling to the muscle activity measurement signal, and generates muscle activity measurement data (S52C). The action state learning apparatus 20C calculates a modeling reference value from the muscle activity measurement data (S53C).

The action state learning apparatus 20C executes learning using the displacement measurement data and the motion measurement data, and the modeling reference value, and generates an action state model (S61C).

It is noted that the above processing may be programmed and stored in a storage medium or the like, and may be executed by an arithmetic processing apparatus, such as a CPU, according to the exemplary configuration as described herein, for example.

The configuration and processing of each of the above exemplary embodiments can be combined as would be appreciated to one skilled in the art. Then, the use of such a combination enables the action state estimation apparatus and the action state estimation method to achieve a higher estimation accuracy. For example, two statistics of the statistic obtained by sampling and the statistic obtained by calculating signal strength distribution are used in combination (i.e., both statistics are used).

In addition, the above description shows an aspect in which a myoelectric sensor (e.g., an electromyograph) is used as the muscle activity detection sensor 102. However, the muscle activity detection sensor 102 may be another sensor configured for measuring muscle activity such as MRI.

Moreover, the above description shows an aspect in which an inertia sensor such as an acceleration sensor or an angular velocity sensor is used as the motion detection sensor 300. However, the motion detection sensor 300 may also use a motion sensor, an imaging sensor, or the like, for example, according to various exemplary aspects.

In addition, the above description shows an aspect in which the displacement measurement signal is sampled. However, when the motion measurement signal is sampled, it is also possible to frequency-sample the displacement measurement signal. However, as described above, by sampling the displacement measurement signal, the action state estimation apparatus is able to estimate the loaded state of a muscle with a higher accuracy.

In view of the foregoing, the displacement detection sensor 101 is preferably a piezoelectric sensor. In other words, while another sensor such as an acceleration sensor improves accuracy by extracting a frequency component, the use of the piezoelectric sensor enables accurate estimation even without such an extraction of a frequency component.

In addition, in the aspect (i.e., the sixth exemplary embodiment) in which the above feature amount is not used, the displacement detection sensor 101 being a piezoelectric sensor functions more effectively.

Moreover, the above configuration and processing show an aspect in which the loaded state of a muscle is estimated as an action state. However, other action states of a test subject who has relevance to the loaded state of the muscle are able to be estimated.

In addition, the above configuration and processing show an aspect in which an action state is estimated by use of the displacement measurement data and the motion measurement data that are obtained by sampling and by adding no change or by use of the displacement statistic and the motion statistic that are obtained by calculating signal strength distribution. However, the action state estimation apparatus and the action state estimation method are also able to use a difference value (e.g., a change amount) or a rate of change of each statistic. Specifically, the action state estimation apparatus and the action state estimation method calculate a difference value (e.g., a change amount) or a rate of change of adjacent statistics in a plurality of statistics, and use a calculated value. Accordingly, the action state estimation apparatus and the action state estimation method are also able to estimate variation in the action state.

In addition, in estimation of a loaded state using the above action state model, the following items related to biological information may be added as an input vector. For example, at least one of the following items: BMI, height, weight, body fat percentage, muscle mass, grip strength (left, right, the first time, the second time), lower thigh minimum circumference, age (20s, 30s, 40s, 50s, 60s), and gender (female, male) of a person to be measured, may be added. As a result, the loaded state of a muscle is able to be estimated with a higher accuracy.

REFERENCE SIGNS LIST

10, 10A, 10B: action state estimation apparatus
11: sampling portion
12: statistic calculation portion
13, 13A, 13B: action state model storage
14, 14A, 14B: estimation calculation portion
20, 20A, 20B: action state learning apparatus
21: sampling portion
22: modeling reference value calculation portion

24, 24A, 24B: learning calculation portion
31: sampling portion
32: statistic calculation portion
101: displacement detection sensor
102: muscle activity detection sensor
300: motion detection sensor

The invention claimed is:

1. An action state estimation apparatus comprising:
a displacement detection sensor configured to detect a displacement measurement signal by converting displacement on a skin surface of a test subject due to tremor and deformation into a voltage that corresponds to the displacement measurement signal;
a storage medium; and
a processing apparatus that includes a first sampling portion configured to sample the displacement measurement signal of the test subject that is detected by the displacement detection sensor and is within a predetermined time and to generate displacement measurement data based on the sampled displacement measurement signal;
an action state model storage configured to store in the storage medium an action state model modeled by associating the displacement measurement data with a loaded state of a muscle of the test subject; and
an estimation calculation portion configured to estimate the loaded state by setting the displacement measurement data as an input vector and using the action state model.

2. The action state estimation apparatus according to claim 1, wherein the action state model sets an importance level according to a time range of the displacement measurement data for each muscle of the test subject of which the loaded state is to be estimated.

3. The action state estimation apparatus according to claim 1, further comprising a second sampling portion configured to sample a motion measurement signal of the test subject within a predetermined time and to generate motion measurement data based on the sampled motion measurement signal.

4. The action state estimation apparatus according to claim 3, wherein:
the action state model storage stores the action state model modeled by associating the displacement measurement data, the motion measurement data, and the loaded state of the muscle of the test subject; and
the estimation calculation portion is configured to estimate the loaded state of the muscle by setting the displacement measurement data and the motion measurement data as the input vector and using the action state model.

5. The action state estimation apparatus according to claim 4, wherein the action state model sets the importance level according to the time range of the displacement measurement data and an importance level based on a time range of the motion measurement data for each muscle of the test subject of which the loaded state is to be estimated.

6. The action state estimation apparatus according to claim 5, wherein the importance level according to the time range of the displacement measurement data and the importance level according to the time range of the motion measurement data are set by a common level of importance.

7. The action state estimation apparatus according to claim 5, wherein the importance level according to the time range of the displacement measurement data and the importance level according to the time range of the motion measurement data are set individually.

8. The action state estimation apparatus according to claim 4, wherein the motion measurement signal is a measurement signal of at least one of acceleration and angular velocity.

9. The action state estimation apparatus according to claim 8, wherein the motion measurement signal includes at least one of an orthogonal triaxial component and a composite component provided by combining the orthogonal triaxial component.

10. The action state estimation apparatus according to claim 1, wherein the input vector includes biological information.

11. The action state estimation apparatus according to claim 1, wherein the estimation calculation portion is configured to set a plurality of statistics as the input vector, with a level of importance of the plurality of statistics set as the action state model and based on a type of the muscle of the test subject to be estimated.

12. An action state estimation method comprising:

detecting, by a displacement detection sensor, a displacement measurement signal by converting displacement on a skin surface of a test subject due to tremor and deformation into a voltage that corresponds to the displacement measurement signal;

sampling the displacement measurement signal of the test subject within a predetermined time and generating displacement measurement data based on the sampled displacement measurement signal; and estimating, by a processing apparatus that executes instructions stored on a storage medium, a loaded state of a muscle of the test subject by using an action state model modeled by associating the displacement measurement data with the loaded state of the muscle and setting the displacement measurement data as an input vector.

13. The action state estimation method according to claim 12, further comprising sampling in time series a motion measurement signal of the test subject within a predetermined time and generating motion measurement databased on the sampled motion measurement signal.

14. The action state estimation method according to claim 13, further comprising:

estimating the loaded state by using the action state model modeled by associating the displacement measurement data, the motion measurement data, and the loaded state of the muscle of the test subject; and setting the displacement measurement data and the motion measurement data as the input vector.

* * * * *